(12) United States Patent
Grossi de Sa et al.

(10) Patent No.: US 8,227,588 B2
(45) Date of Patent: Jul. 24, 2012

(54) COMPOSITIONS AND METHODS FOR MODIFYING GENE EXPRESSION USING THE PROMOTER OF UBIQUITIN CONJUGATING PROTEIN CODING GENE OF COTTON PLANTS

(75) Inventors: Maria Fatima Grossi de Sa, Brasilia-DF (BR); Luciane Mourão Guimarães, Brasilia-DF (BR); João Aguiar Nogueira Batista, Brasilia-DF (BR); Antonio Américo Barbosa Viana, Brasilia-DF (BR); Rodrigo da Rocha Fragoso, Brasilia-DF (BR); Thales Lima Rocha, Brasilia-DF (BR)

(73) Assignee: Empresa Brasileira de Pesquisa Agropecuaria, Brasilia-DF (BR)

( * ) Notice: Subject to any disclaimer, the term of this patent is extended or adjusted under 35 U.S.C. 154(b) by 820 days.

(21) Appl. No.: 12/017,309

(22) Filed: Jan. 21, 2008

(65) Prior Publication Data
US 2009/0320153 A1    Dec. 24, 2009

(30) Foreign Application Priority Data
Feb. 5, 2007    (BR) .................................... 0701230

(51) Int. Cl.
*C12N 15/82*    (2006.01)
*C12N 15/63*    (2006.01)
*A01H 5/00*    (2006.01)
*C07H 21/04*    (2006.01)

(52) U.S. Cl. ...... 536/24.1; 536/23.1; 800/278; 800/295; 435/320.1; 435/468

(58) Field of Classification Search .................. None
See application file for complete search history.

(56) References Cited

U.S. PATENT DOCUMENTS

| | | | |
|---|---|---|---|
| 5,510,474 A | 4/1996 | Quail et al. | |
| 5,614,399 A | 3/1997 | Quail et al. | |
| 5,723,765 A * | 3/1998 | Oliver et al. ................. | 800/268 |
| 5,753,475 A | 5/1998 | Houck | |
| 6,020,190 A | 2/2000 | Quail et al. | |
| 6,391,639 B1 | 5/2002 | Schenk et al. | |
| 6,441,273 B1 | 8/2002 | Aldwinckle et al. | |
| 6,489,462 B1 | 12/2002 | Olszewski et al. | |
| 6,528,701 B1 | 3/2003 | Wang et al. | |
| 6,670,467 B2 | 12/2003 | Barbour et al. | |
| 6,677,505 B1 | 1/2004 | Esnault et al. | |
| 6,706,948 B1 | 3/2004 | Albert et al. | |
| 2002/0115850 A1 | 8/2002 | Chung et al. | |
| 2002/0152501 A1 | 10/2002 | Fischer et al. | |
| 2003/0066108 A1 | 4/2003 | Jilka et al. | |
| 2003/0175783 A1 | 9/2003 | Waterhouse et al. | |
| 2006/0143735 A1 | 6/2006 | Medrano et al. | |

FOREIGN PATENT DOCUMENTS

| | | |
|---|---|---|
| WO | WO 8903887 | 5/1989 |
| WO | WO 8910396 | 11/1989 |
| WO | WO 9213956 | 8/1992 |
| WO | WO 9519443 | 7/1995 |
| WO | WO 9713865 | 4/1997 |
| WO | WO 98/30698 | 7/1998 |
| WO | WO 01/94394 A2 | 12/2001 |
| WO | WO 01/94394 A3 | 12/2001 |
| WO | WO 03102198 | 12/2003 |

OTHER PUBLICATIONS

Database EMBL [Online], "GH_MBb0050B04f GH_MBb Gossypium hirsutum genomic clone GH_MBb0050B04f, genomic survey sequence," (2006) XP002476851 retrieved from EBI accession No. EMBL:DX540525 Database accession No. DX540525.
Database EMBL [Online], "Gossypium hirsutum cultivar Acala SJ2 calmodulin-binding heat shock protein gene, complete cds," (2006) XP002476852 retrieved from EBI accession No. EMBL:AY628138, Database accession No. AY628138.
Hatfield, et al., "The ubiquitin-activating enzyme (E1) gene family in *Arabidopsis thaliana*" Plant Journal (1997) 11(2):213-226. XP002476847 ISSN: 0960-7412.
Hill-Ambroz, et al., "Constitutive promoter expression of transgens in wheat (Triticum Aestivum)," Cereal Research Communications (2001) 29(1/2):9-16. XP001153700, ISSN: 0133-3720.
Holtorf, et al., "Comparison of different constitutive and inducible promoters for the overexpression of transgenes in *Arabidopsis thaliana*," Plant Molecular Biology, Springer. Dordrecht. NI. (1995) 29:637-646, XP002036874, ISSN: 0167-4412.
Kang, et al., "Comparing constitutive promoters using CAT activity in transgenic tobacco plants," Molecules and Cells, (2003) 16(1):117-122, XP002476849, ISSN: 1016-8478.
Thoma et al., "Members of two gene families encoding ubiquitin-conjugating enzymes. AtUBCI-3 and AtUBC4-6, from *Arabidopsis thaliana* are differentially expressed," Plant Molecular Biology (1996) 31(3):493-505. XP002476848 ISSN: 0167-4412.
Zhang, et al, "Molecular cloning, differential expression, and functional characterization of a family of class I ubiquitin-conjugating enzyme (E2) genes in cotton (Gossypium)," Biochimica Et Biophysica Acta, (2003) 1625(3): 269-279, XP002476850 ISSN: 0006-3002.
European Search Report dated Apr. 17, 2008, for European Application No. EP 08 00 2062.
Binet et al., "Analysis of a sunflower polyubiquitin promoter by transient expression," Plant Science, (1991) 79: 87-94.
Callis et al., "Ubiquitin extension proteins of *Arabidopsis thaliana*, "J. Biol. Chem., (1990) 265(21): 12486-93.
Callis et al., "Ubiquitin and Ubiquitin Genes in Higher Plants," Oxford Surveys of Plant Molecular & Cell Biology, (1989) 6: 1-30.
Christensen et al., "Maize polyubiquitin genes: structure, thermal perturbation of expression and transcript splicing, and promoter activity following transfer to protoplasts by electroporation," Plant Molecular Biology, (1992) 18(4): 675-689.

(Continued)

Primary Examiner — Brent T Page
(74) Attorney, Agent, or Firm — Knobbe Martens Olson & Bear LLP

(57) ABSTRACT

The present Invention relates to regulatory sequences of polynucleotides isolated from cotton plants capable of initiating and activating the transcription of polynucleotides, and the use of these regulatory sequences for modifying the transcription of endogenous and/or heterologous polynucleotides and the production of polypeptides.

24 Claims, 14 Drawing Sheets

OTHER PUBLICATIONS

Clough et al., "Floral dip: a simplified method for Agrobacterium-mediated transformation of *A. thalianam*" *Plant J.*, (1998)16(6):735-43.

Fraley et al., "Expression of bacterial genes in plant cells," *Proc. Natl. Acad. Sci. USA*, (1983) 80(15):4803-7.

Fromm et al., "Expression of genes transferred into monocot and dicot plant cells by electroporation," *Proc. Natl. Acad. Sci. USA*, (1985) 82:5824-5828.

Genschik et al., "Structure and promoter activity of a stress and developmentally regulated polyubiquitin encoding gene of *Nicotiana tabacum*," *Gene*, (1994) 148(2): 195-202.

Keil et al., "Both wound-inducible and tuber-specific expression are mediated by the promoter of a single member of the potato proteinase inhibitor II gene family," *EMBO J.*, (1989) 8(5):1323-1330.

Keller et al., "Glycine-rich cell wall proteins in bean: gene structure and association of the protein with the vascular system," *EMBO J.*, (1988) 7(12):3625-3633.

Keller et al., "Specific expression of a novel cell wall hydroxyproline-rich glycoprotein gene in lateral root initiation," *Genes Devel.*, (1989) 3(10):1639-1646.

Miles et al., "Complete nucleotide sequence of the fumarase gene fumA, of *E. coli*," *Nucleic Acids Res.*, (1984) 12(8):3631-3642.

Paszkowski et al., "Direct Gene Transfer to Plants" *Embo. J.*, (1984) 3(12):2717-2722.

Schmülling et al., "Promoters of the *rolA, B*, and C Genes of *Agrobacterium rhizogenes* Are Differentially Regulated in Transgenic Plants," *Plant Cell*, (1989) 1(7):665-670.

* cited by examiner

```
Arabidopsis              ------------------------------------------------------------
Uce_Oryza_3              ------------------------------------------------------------
Gos-2_Zea                ------------------------------------------------------------
Uce_Oryza_1              ------------------------------------------------------------
A-Tubulin_Coffea_1       --------------------------------------------AAAAGTTGTAGCGGGA  16
Uce_Oryza_4              ------------------------------------------------------------
UBI9_Saccharum           ------------------------------------------------------------
Enolase_Zea              ------------------------------------------------------------
Actin-2_Zea              ------------------------------------------------------------
Uce_Oryza_2              CTGCAGAAATGCAAATTTCATAAAACAAACTACTAGTACTGTTTGTTCATTGGTCTTATC  60
UceA1.7                  ------------------------------------------------------------
A-Tubulin_Coffea_2       ------------------------------------------------------------
35Sd_AMV                 ------------------------------------------------------------

Arabidopsis              ----------------------------------------------------------
Uce_Oryza_3              ----------------------------------------------------------
Gos-2_Zea                ----------------------------------------------------------
Uce_Oryza_1              ----------------------------------------------------------
A-Tubulin_Coffea_1       GGGCTGGACGATGCGTGGAGCGGAAAATGCTGGAGTATTGGACCACCAACCAAACAAAAT  76
Uce_Oryza_4              ----------------------------------------------------------
UBI9_Saccharum           ----------------------------------------------------------
Enolase_Zea              ----------------------------------------------------------
Actin-2_Zea              ----------------------------------------------------------
Uce_Oryza_2              CAAAACTTAGCCACTGCAACAAGTTCTTGAACCTTAGCACAATCATATTGTGCATGCACT  120
UceA1.7                  ----------------------------------------------------------
A-Tubulin_Coffea_2       ----------------------------------------------------------
35Sd_AMV                 ----------------------------------------------------------

Arabidopsis              ----------------------------------------------------------
Uce_Oryza_3              ----------------------------------------------------------
Gos-2_Zea                ----------------------------------------------------------
Uce_Oryza_1              ----------------------------------------------------------
A-Tubulin_Coffea_1       AGTTTTAGTATATGGGGTTTCGAACTTTCCAGTCAACCTACAACAATCTGCTTCTATAAA  136
Uce_Oryza_4              ----------------------------------------------------------
UBI9_Saccharum           ----------------------------------------------------------
Enolase_Zea              ----------------------------------------------------------
Actin-2_Zea              ----------------------------------------------------------
Uce_Oryza_2              TGTTTATTGCAAAGAATGGTGCGTAGGGAACACGCATGATTTTTGAATTGCTGGCACATA  180
UceA1.7                  ----------------------------------------------------------
A-Tubulin_Coffea_2       ----------------------------------------------------------
35Sd_AMV                 ----------------------------------------------------------

Arabidopsis              ----------------------------------------------------------
Uce_Oryza_3              ----------------------------------------------------------
Gos-2_Zea                ----------------------------------------------------------
Uce_Oryza_1              ----------------------------------------------------------
A-Tubulin_Coffea_1       CAATAATAAAAGAGTAACTAAAATTACTGGTAGCGTTGGTGTATTTGGATTTGCCAGCTTT  196
Uce_Oryza_4              ----------------------------------------------------------
UBI9_Saccharum           ----------------------------------------------------------
Enolase_Zea              ----------------------------------------------------------
Actin-2_Zea              ----------------------------------------------------------
Uce_Oryza_2              ATTTTATCATTAGAAACTGGAATGCAACATGTACCCTTTGTCATGGTTTCTTTCCGAGAC  240
UceA1.7                  ----------------------------------------------------------
A-Tubulin_Coffea_2       ----------------------------------------------------------
35Sd_AMV                 ----------------------------------------------------------

Arabidopsis              ----------------------------------------------------------
Uce_Oryza_3              ----------------------------------------------------------
Gos-2_Zea                ----------------------------------------------------------
Uce_Oryza_1              ----------------------------------------------------------
A-Tubulin_Coffea_1       GCTTCCAAACTCATATCATCAATTTGATAGCACTTGGATACGGAGATCGCTTTTGTCTGC  256
Uce_Oryza_4              ----------------------------------------------------------
UBI9_Saccharum           ----------------------------------------------------------
Enolase_Zea              ----------------------------------------------------------
Actin-2_Zea              ----------------------------------------------------------
Uce_Oryza_2              ATTGCACTGTTTTTTTTAATCCTATCATTATCATAATGCCAAGAACTGGTCACCAACCAG  300
UceA1.7                  ----------------------------------------------------------
A-Tubulin_Coffea_2       ----------------------------------------------------------
35Sd_AMV                 ----------------------------------------------------------

Arabidopsis              ----------------------------------------------------------
Uce_Oryza_3              ----------------------------------------------------------
```

FIGURE 3A

```
Gos-2_Zea                 ------------------------------------------------------------
Uce_Oryza_1               ------------------------------------------------------------
A-Tubulin_Coffea_1        CTTAGTATGATATGATTGCTCACCCGCTGTAGACATGATTTAAAGGAAAATAACACAAAT 316
Uce_Oryza_4               ------------------------------------------------------------
UBI9_Saccharum            ------------------------------------------------------------
Enolase_Zea               ------------------------------------------------------------
Actin-2_Zea               ------------------------------------------------------------
Uce_Oryza_2               CATTTTGCATCATGGTTAGTTGAGCTGTCCCCATGTATCAATAGGTGCATTGTATTGGTC 360
UceA1.7                   ------------------------------------------------------------
A-Tubulin_Coffea_2        ------------------------------------------------------------
35Sd_AMV                  ------------------------------------------------------------

Arabidopsis               ------------------------------------------------------------
Uce_Oryza_3               ------------------------------------------------------------
Gos-2_Zea                 ------------------------------------------------------------
Uce_Oryza_1               ------------------------------------------------------------
A-Tubulin_Coffea_1        ATATATATATAAGACCAACAAATTATAACTGAAAACTTTTCAGTAATGTTAATTCTAACA 376
Uce_Oryza_4               ------------------------------------------------------------
UBI9_Saccharum            ------------------------------------------------------------
Enolase_Zea               ------------------------------------------------------------
Actin-2_Zea               ------------------------------------------------------------
Uce_Oryza_2               CAAAATATAAATGCAGTGGATGCAACCTATCTCATGGCCGTCAACAAAAGAAATCAAAAG 420
UceA1.7                   ------------------------------------------------------------
A-Tubulin_Coffea_2        ------------------------------------------------------------
35Sd_AMV                  ------------------------------------------------------------

Arabidopsis               ------------------------------------------------------------
Uce_Oryza_3               ------------------------------------------------------------
Gos-2_Zea                 ------------------------------------------------------------
Uce_Oryza_1               ------------------------------------------------------------
A-Tubulin_Coffea_1        CATGTGACTAGACCTGCTATCATCAGCTGCAATTCTAGAGGAAACTTGGACCAGATCAGA 436
Uce_Oryza_4               ------------------------------------------------------------
UBI9_Saccharum            ------------------------------------------------------------
Enolase_Zea               ------------------------------------------------------------
Actin-2_Zea               ------------------------------------------------------------
Uce_Oryza_2               GGAAATGCACCATCTTATATCTCCAGTTTATATGAACAGATTGGATAAGATCATAAGATC 480
UceA1.7                   ------------------------------------------------------------
A-Tubulin_Coffea_2        ------------------------------------------------------------
35Sd_AMV                  ------------------------------------------------------------

Arabidopsis               ------------------------------------------------------------
Uce_Oryza_3               ------------------------------------------------------------
Gos-2_Zea                 ------------------------------------------------------------
Uce_Oryza_1               ------------------------------------------------------------
A-Tubulin_Coffea_1        AGTTGTAAAGGGCTGCAGTCCATTCCTGCACTATTCAGTTTGCAGGTAGATGGGTGGACC 496
Uce_Oryza_4               ------------------------------------------------------------
UBI9_Saccharum            ------------------------------------------------------------
Enolase_Zea               ------------------------------------------------------------
Actin-2_Zea               ------------------------------------------------------------
Uce_Oryza_2               AAGTGGTTTATATTATTTTGAGGAATATAACATGGATTCATCCTAATCACTCGTCTAGGC 540
UceA1.7                   ------------------------------------------------------------
A-Tubulin_Coffea_2        ------------------------------------------------------------
35Sd_AMV                  ------------------------------------------------------------

Arabidopsis               ------------------------------------------------------------
Uce_Oryza_3               ------------------------------------------------------------
Gos-2_Zea                 ------------------------------------------------------------
Uce_Oryza_1               ------------------------------------------------------------
A-Tubulin_Coffea_1        ATTATATGGATCTGGTCCAGCGTGAATGCAGTTGTAGTAAAGACATGTTGGATTTGTTAT 556
Uce_Oryza_4               ------------------------------------------------------------
UBI9_Saccharum            ------------------------------------------------------------
Enolase_Zea               ------------------------------------------------------------
Actin-2_Zea               ------------------------------------------------------------
Uce_Oryza_2               AGTATGTGTATTCATGATGGATATGGTACTATACTACGGAGTTTTTTCTTCACAAAATAA 600
UceA1.7                   ----------------------------------------AGTGAAGTAGCAGAGATAATAG 22
A-Tubulin_Coffea_2        ------------------------------------------------------------
35Sd_AMV                  ------------------------------------------------------------
```

FIGURE 3B

```
Arabidopsis        ------------------------------------------------------------
Uce_Oryza_3        ------------------------------------------------------------
Gos-2_Zea          ------------------------------------------------------------
Uce_Oryza_1        ------------------------------------------------------------
A-Tubulin_Coffea_1 GGATCAAACTACTACTAGTAGGGAAATGCTTCAAAGACTTCTCTTGTGATTTTCTCCCAG 616
Uce_Oryza_4        ------------------------------------------------------------
UBI9_Saccharum     --------------------GAATTCCGGCGTGGGCGCTGGGCTAGTGCTCCCGCAGCGA 40
Enolase_Zea        ------------------------------------------------------------
Actin-2_Zea        ------------------------------------------------------------
Uce_Oryza_2        CCTGTTATTTTGACCTCCAACCAAACACGAATTATACCAAAAATTGGGTTATTTCATCTA 660
UceA1.7            TTATTACAGTAGCAGTAATAAAATAAAATACATTTTATTACAAAAAAACGTACAAGAGGT 82
A-Tubulin_Coffea_2 ------------------------------------------------------------
35Sd_AMV           ------------------------------------------------------------

Arabidopsis        ------------------------------------------------------------
Uce_Oryza_3        ------------------------------------------------------------
Gos-2_Zea          ------------------------------------------------------------
Uce_Oryza_1        ------------------------------------------------------------
A-Tubulin_Coffea_1 CCGAATGGTCCAAGTACACTAGCAAAAGAAGCACAAACGGTACCAATGACTCGAGCGAGC 676
Uce_Oryza_4        ------------------------------------------------------------
UBI9_Saccharum     GCGATCTGAGAGAACGGTAGAGTTCCGGCCGGGCGCGCGGGAGAGGAGGAGGGTCGGGCG 100
Enolase_Zea        ------------------------------------------------------------
Actin-2_Zea        ------------------------------------------------------------
Uce_Oryza_2        TAGTACAACTCTATTATAAACATGCAGTAAATTATCCTACACATATACCAAAATTCAAGT 720
UceA1.7            CCGCGAAGATAGCCAATGAGAACGCAAGAAGACAACCCAATTCT-CCTATTTTTTTATTA 141
A-Tubulin_Coffea_2 ------------------------------------------------------------
35Sd_AMV           ------------------------------------------------------------

Arabidopsis        ------------------------------------------------------------
Uce_Oryza_3        ------------------------------------------------------------
Gos-2_Zea          ------------------------------------------------------------
Uce_Oryza_1        ------------------------------------------------------------
A-Tubulin_Coffea_1 TGACATTTTGGGCTTCAGATTAGCACAAGACAAAAGGATTTTTCACTTTTCTTCTGTAGG 736
Uce_Oryza_4        ------------------------------------------------------------
UBI9_Saccharum     GGGAGGATCCGATGGCCGGGAACGAGTGGATCAATGGGTACCTGGAGGCGATCCTCGACA 160
Enolase_Zea        ------------------------------------------------------------
Actin-2_Zea        ------------------------------------------------------------
Uce_Oryza_2        GTAATAATCCTAATACACAGACTTAAAAATCAAACTATTTCCTTTTTAAGTATATGGAAA 780
UceA1.7            AATATTTCTAGAAGAAAGGGTAAATTACGCCCCACGGTCACAAAACTATTAATAAGATCA 201
A-Tubulin_Coffea_2 ----------------CATTTCTTGCCAGAAAGCACTAGTGAATATTCTATCCCTGTCAG 44
35Sd_AMV           ------------------------------------------------------------

Arabidopsis        ------------------------------------------------------------
Uce_Oryza_3        ------------------------------------------------------------
Gos-2_Zea          ------------------------------------------------------------
Uce_Oryza_1        ---------------------GTCGACCTGATGATTATTTTGTTGATCATGATTTTCTTT 39
A-Tubulin_Coffea_1 TGATCCTGGACTCGCAGGTTGGCATGCTCAATTCAGGAGCTTCTGAGATTGGATAGGGTG 796
Uce_Oryza_4        ------------------------------------------------------------
UBI9_Saccharum     GCCACACCTCGTCGCGGGGTGCCGGCGGCGGCGGCGGCGGGGGGGACCCCAGGTCGCCGA 220
Enolase_Zea        ------------------------------------------------------------
Actin-2_Zea        ------------------------------------------------------------
Uce_Oryza_2        CCATTTTTTTAACGGAAGGAAAACAAATTCGGGTCAAGGCGGAAGCCAGCGCGCCACCCC 840
UceA1.7            TATATTTATCACTCAACTTCCAAAAGTTACAAAATGATTATTAAACTATTCAAAAGTTTT 261
A-Tubulin_Coffea_2 TCACTATAGATTCTGGAAGTCCATGTAATCTAAAAATGTTTCCAGGAAGAGTTGAGCCAC 104
35Sd_AMV           ------------------------------------------------------------

Arabidopsis        ----------GTGTTCATTTGATAGAGTCTAAAATCACCACTTACATTGACTAACCCCAA 50
Uce_Oryza_3        ------------------------------------------------------------
Gos-2_Zea          ------------------------------------------------------------
Uce_Oryza_1        TGGCTATTTGATTTTTTGAAAGATATTTTTTTCCCTGGGAAGACACCTATGGGACGAAGA 99
A-Tubulin_Coffea_1 TTGGTTATGAATGCACCGCAGGTTGCATGCTCAATTCAGAGCCCTTCACATGTAACCGTG 856
Uce_Oryza_4        ------------------------------------------------------------
UBI9_Saccharum     CGAAGGCGGCGAGCCCCCGCGGC-GCGCACATGAACTTCAACCCCTCGCACTACTTCGTC 279
Enolase_Zea        ------------------------------------------------------------
Actin-2_Zea        ------------------------------------------------------------
Uce_Oryza_2        ACGTCAGCGAATACGGAGGCGCGGGGTTGACGGCGTCACCCGGTCCTAACGGCGACCAAC 900
UceA1.7            ATTTCAAGTCATTGGATTGTTAAAATAGCATTTGTATGGATTTCCCTGTTCACATTGCCT 321
A-Tubulin_Coffea_2 CTGTTTGGTTGTGAAGGGGTGAGCTAAGGCAAGCAAATGACCTACTTTGGACAACCTATC 164
35Sd_AMV           ------------------------------------------------------------
```

FIGURE 3C

```
Arabidopsis        AAATTTGTCCTAAACACTAATCAATCCGAAGATTATAAAATGTCGACAAAGAAAATAAAA 110
Uce_Oryza_3        ------------------------------------------------------------
Gos-2_Zea          ------------------------------------------------------------
Uce_Oryza_1        TATTATGTTATATATATATATATATATATATATATATATATATATATATATATATATATA 159
A-Tubulin_Coffea_1 TGTAGCCCAGGCCCAAATGCCCCGGAAYTTTAAACTGAAATCTCGGAAYAGCAGATGGCA 916
Uce_Oryza_4        ------------------------------------------------------------
UBI9_Saccharum     GAGGAGGTGGTCAAGGGCGTCGACGAGAGCGACCTCCACCGGACGTGGATCAAGGTCGTC 339
Enolase_Zea        ---------------------------------------------TCATATATTTATG 13
Actin-2_Zea        -------------------------------------------------------TCAGT 5
Uce_Oryza_2        AAACCAGCCAGAAGAAATTACAGTAAAAAAAAGTAAATTGCACTTTGACCCACCTTTTAT 960
UceA1.7            ACATCAATCGAAGCCTCTCATTCCCCTTCTTTTTTATAGATTAAGTTTTTTTTATAAAA 381
A-Tubulin_Coffea_2 AATCACGTATTATATCCTTGAGATTCTGGAAGGCTCTCTATGAAGTCCATGGTTAGGTGA 224
35Sd_AMV           ---------------------------------------------GGTCCGATCTGAG 13

Arabidopsis        TAAAATAGGAGTCTATGAGTCGATGGAACTTATCCAACTAAACTTTAATAAGAATGAACC 170
Uce_Oryza_3        ------------------------------------------------------------
Gos-2_Zea          ------------------------------------------------------------
Uce_Oryza_1        TATATATCACATCAGTCTCTGCACAAAGTGCATCCTGGGCTGCTTCAATTATAAAGCCCC 219
A-Tubulin_Coffea_1 ACGGTCGTAATTCGTCAAGCAATCCGAAACGTCGCCACACCCCCACGCCAGCTGGAAAAT 976
Uce_Oryza_4        -----------------------------AAGCTTGTCTGTCTCTACTAGATACCAGGGTTTC 34
UBI9_Saccharum     GCCACCCGCAACGCCCGCGAGCGCAGCACCAGGCTCGAGAACATGTGCTGGCGGATCTGG 399
Enolase_Zea        AACGGAGATAGTGCATCTATCATGCGATTCTTCGACGGAGTCGACGTCTGATTGGACCAG 73
Actin-2_Zea        ATGATTGCTTTCAATATAGGCTGATGGAGCCTATGAATGATCTATAACTATGTGATTGGA 65
Uce_Oryza_2        TACCCAAAGTTTCAATTTGGACCACCCTTAAACCTATCTTTTCAAATTGGGCCGGGTTGT 1020
UceA1.7            CAATTTTAAACATCATGAATCTCTGAACTAAAATTTAAATAACTTTTTTCTTCGATCTTT 441
A-Tubulin_Coffea_2 GTCCAAGCTAAACGAGGAATAGGTGATGGTTGTAGCAGTCCAAGGTAGGGTCCATGCTTT 284
35Sd_AMV           ACTTTTCAACAAAGGGTAATATCGGGAAACCTCCTCGGATTCCATTGCCCAGCTATCTGT 73

Arabidopsis        AAACTCAATTTT--GTAATAATATTTAAAATACGTT---TTTACTCTCTCCCAGA---AT 222
Uce_Oryza_3        ------------------------------------------------------------
Gos-2_Zea          -------------------ATTATTGGCTGTAGGAT----TCTAAACCGAGCCTAA---AT 35
Uce_Oryza_1        ATTCACCACATT--TGCGAGATAGTCGAAAAGCACCA--TCAATATTGAGCTTCAGGTAT 275
A-Tubulin_Coffea_1 CAGTTCAAAATT--CAAAATTCATTTTGGAGCCGTTC--AAACAAAATTGTTTCAGTTTT 1032
Uce_Oryza_4        ATCTTTCGGTTT--GGTCATTTGGACCAGGGTGCCCG--AAATATCGAAATTTCAGAAAT 90
UBI9_Saccharum     CACCTCGCGCGCAAGAAGAAGCAGCTGGAGCTGGAGG--GCATCCAGAGAATCTCGGCAA 457
Enolase_Zea        AATTTCAGATGGTGAGCAAAAGTGCCACTTGCCTGCC--TCCTTTTCTCGTGCCTGCCTC 131
Actin-2_Zea        TGTCTTAACTTGCGTAGCCAAGCTCGTATGAGCCTCT--TTTACTGGGTACCACTAATTT 123
Uce_Oryza_2        GGTTTGGACTACCATGAACAACTTTTCGTCATGTCTAACTTTCCGGCCAAACATATG 1080
UceA1.7            GACATTGAATGTTAAATTAACTTGAATCTAAGGTATG-TTCTACTTGTTGATAAATACAG 500
A-Tubulin_Coffea_2 GACTTAAATCTTTGGCATATGTCACAAGCATGAATATACCTGATGATTTTCCCCAAATGT 344
35Sd_AMV           CACTTCATCAAAAGGACAGTAGAAAAGGAAGGTGGCACCTACAAATGCCATCATTGCGAT 133

Arabidopsis        ATCCCATCTCTCTGATTCCAATTCCTCCTCTCTCTCT---TTCGTCTCTCTAC------- 272
Uce_Oryza_3        --------------------AAGCTTTGCTCCGTGTCT---GCTTGGGCCATAT------- 31
Gos-2_Zea          AGCTGGAATAGCT--CTATAGCCCTCAATCCAAACTA---ATGATATCTATAC------- 83
Uce_Oryza_1        TTTTGGTTGTGTTGTGGGTTGGATTGAGTCCGATATAT---ACCAAATCAATATA----AT 328
A-Tubulin_Coffea_1 GCCCCTCGCCTGCTGCCCTAATCTTACCCGCCATTG---GGGCTTGGATTACTC----GC 1086
Uce_Oryza_4        TTCGGTTCGAAATTATATGAATTTTTGAACAAAATTT---GATTAAATTAAACAA---AA 144
UBI9_Saccharum     GAAGGAAGGAACAGGAGCAGGTGCGTCGTGAGGCGAC---GGAGGACCTGGCCGA---GG 511
Enolase_Zea        AAGGATAGAAAGAAAGGAGAACAATATACTATTTAA---GATCAGATAAAAATAT---TA 185
Actin-2_Zea        CTATATATTAGATACAGTTAAATA--AGTCTAAATTA---CATCGGTGCGTGCG----TG 174
Uce_Oryza_2        AACCATATATAGAGGAGATCGGCCGTATACTAGAGCT---GATGTGTTTAAGGTC----GT 1134
UceA1.7            ATCCATCGTGTTGATCATTGAATCGTCACTTGGAGCT---CACTCATCGGACTTAAA-AA 556
A-Tubulin_Coffea_2 TTTTGAGGTTTTTAATACCGGGAATGGCCCAGGAAAAAGGGCCCTGGCTTTGCACCAAGG 404
35Sd_AMV           AAAGGAAAGGCTATCGTTCAAGATGCCTCTGCCGACAGTGGTCCCAAAGATGGAC---CC 190

Arabidopsis        CCCGAATTGATTGTTTTAACCCCCGGTGATCGGAGCAAACTCT--CTGACGGTGACCGCC 330
Uce_Oryza_3        AC---ACGGACCAGCCCAATAGCCAGAAGCCTGT---AGCTCT--CC-ATGG-----GCC 77
Gos-2_Zea          TTATGCAACTCTAAATTTTTATTCTAAAAGTAATATTTCATTT--TTGTCAACGAGATTC 141
Uce_Oryza_1        TCACTACGGAATATACCATAGCCATCACAACTTTATTAATTTTGGTAGCTTAAGATGGTA 388
A-Tubulin_Coffea_1 TCCAGTCTATATATATAACTCCCTCCCGCATTGCCTCACCACACGACCCCAAGTCCTCTC 1146
Uce_Oryza_4        TATTATCAGATTTGCAAAAAATATGAAAAAAAAATCGGTCGAAATAATGTCGTATCTGGG 204
UBI9_Saccharum     ATCTGTCAGAA--GGCGAGAAGGGAGACACCATCGGCGAGCTTGCGCCGGTTGAGAC-GAC 569
Enolase_Zea        TAAGTCAAGGATAGAAAGAAAGGAGAAACAATATACTATTTAAGCATCAGATAAAAAAGA 245
Actin-2_Zea        CCAGTACGACTAGATGTAGTGAACTAAACACAGGTTAAGCTGTGATCAATGTA---TGTA 231
Uce_Oryza_2        TGATTGCACGAGAAAAAAAATCCAAATCGCAACAATAGCAAATTTATCTAGTTCAAAGT 1194
UceA1.7            AAAAACCTTAACAACCTAGTGACTTAAATAAAACTTTTGAATAGTTTACTGACTATTTTG 616
A-Tubulin_Coffea_2 TCCCCTAAGAATTTCTGGCAAAGTTCAAGCGGTTCCAAAGTGCCCCAATGGGACCTCTC 464
35Sd_AMV           CCACCCACGAGGAGCATCGTGGAAAAAGAAGACGTTCCAACCACGTCTTCAAAGCAAGTG 250
```

FIGURE 3D

```
Arabidopsis         GGTGATC--ATTT-TTTGTGAACTTCACTTT---TGGTAAGCAGCTT--TGACTTT-TGT 381
Uce_Oryza_3         CGTACTC--GTGC-CACGTG----TCAATCC---TGTGGTTCGGTTTCGTGGCGGT-TGC 126
Gos-2_Zea           TCTACTCT-ATTC-CACAATCTTTTGAAGCTATATTTACCTTAAATCTGTACTCTA-TAC 198
Uce_Oryza_1         TATATAAT-AACC-AATTAACAACTGATTCTAATTTTACTACGGCCCAGTATCTAC-CAA 445
A-Tubulin_Coffea_1  CTTCTTCTCCTTT-CCCAGATCTCGGAGGTCTCTCACTCTTCCGATCCAGAGACGT-CTT 1204
Uce_Oryza_4         TTCGATCCGAAAT-TTTGAACCCATGCTAGCTGCCAGGCTTTGGATTCTGAGCGTCACGT 263
UBI9_Saccharum      CAAGAAGAAGTTC-CAGAGGAACTTCTCTGACCCTTACCGTCTGGTCTGACGACAAT-AAG 627
Enolase_Zea         GCTAATA--ATTT-TTTGGGACACATATACTGGTTACATTGTTATAATCTGTATATATCA 302
Actin-2_Zea         GAGAGTCTGACTC-TTTATATGCGGACAACTAAACACACGATAAGTGTCGAGAATGATTG 290
Uce_Oryza_2         GAAAAGATATGTT-TAAAGGTAGTCCAAAGTA---AAACTTAGGGGCTGTTTGGTTCCCA 1250
UceA1.7             TAACTTTTTAAAG-TTAAGTGACTAAAACGTGAACATACTAATAGTTTAGTGACCTCGGA 675
A-Tubulin_Coffea_2  CAAAAAAGGTGCCCCGGGGACAAGTTGTGCTCAGTTCGGCGCGTTTCAAGACAGGTTTTG 524
35Sd_AMV            GATTGATGTGATGGTCCGATCTGAGACTTTTCAACAAAGGGTAATATCGGGAAACCTCCT 310

Arabidopsis         TC-ATAATCCT-TCACTTTTACTTT----TCAATTTT-GCTTTTTCC-TCTG----ATCT 429
Uce_Oryza_3         GT-TTCCTCCTCTCTCTTTTCTTTT----TCATCTTT-TTTTTTTCT-TACG----ACAT 175
Gos-2_Zea           CA-ATAATCAT--ATATTCTATTAT----TTATTTTTATCTCTCTCC-TAAGGAGCATCC 250
Uce_Oryza_1         TACAAAACAACGAGTATGTTTTCTT----CCGTCGTAATCGTACACAGTACAAAAAAACC 501
A-Tubulin_Coffea_1  TGTATACGCCTCTGGTATCTCCATT----CCTCCTTTTTCCCTCTCTTCCAAAAATCTCC 1260
Uce_Oryza_4         CAGGCACAATAAAATATTTGGGCCT----CTAACTCTTCGTGGGCTGATCTGGGCCGTAG 319
UBI9_Saccharum      GAGAAGAAGCTTTACATTGGTCTCA----TCAGCGTG-CATGGTCTTGTTCGTGGAGAAA 682
Enolase_Zea         CG-TTGTTCGAATATATTCCAAATT----TTTACTATGATTCGTGCTCTACCGGAACTAC 357
Actin-2_Zea         AGGAAATATTGGTCGTTCCACGTGA-----TTGAGTAAGAATGAGAGGGAAATAAAAGGAT 346
Uce_Oryza_2         GCCATACTTTACCATTACTTGCCAA-----CAAAAGTTGCCACACCTTGTCTAAGGTGAGG 1306
UceA1.7             TGATTTTACCCAAAAAATTATTATT----CAACCTCTCGTCCTCTCCTTTTTACACCTTT 731
A-Tubulin_Coffea_2  GCCAGAAAGCAAGGGGTTCCAAAGGG--TGTCAGAGGGTCCATGTTTCAAAACTCCGGG 582
35Sd_AMV            CGGATTCCATTGCCCAGCTATCTGTCACTTCATCAAAAGGACAGTAGAAAAGGAAGGTGG 370

Arabidopsis         GATCTTAGTT------ATTAAGCTGTTGAATCGCATGATCCTTTC----TTCTCTGATTGA 480
Uce_Oryza_3         T-TATAGGTT-----TCGTAGCGGCTGCGTTCCTATTTTCCTT----TTCTTTTTCTAT 225
Gos-2_Zea           CCCTATGTCT-----GCATGGCCCCCGGGTCGGGTCCCAATCTC----TTGCTCTGCTAG 301
Uce_Oryza_1         TGGCCAGCCT-----TTCTTGGGCTGGGGCTCTCTTTCCGAAACG----TCACAAAACGTA 552
A-Tubulin_Coffea_1  TATTCATTTC-----TCAAAACATCGCGAAAATGAGAGAGTGCA----TCTCCATCCATA 1311
Uce_Oryza_4         CAGACGAGAG-----ACGCCATGACACGATCTCATCAATTCCGTAG--TGGCCACGGAAC 372
UBI9_Saccharum      ACATGGAACT-----AGGTCGTGATTCTGATACAGGTGGCCAGGTGAAATATGTGGTCGA 737
Enolase_Zea         TTCTAGATTT-----TGAAAACTTTATGAGAATTTTCTTATTTAG---ATACACTAAGGC 409
Actin-2_Zea         TTGGTGCGTTG---GTTTTGAAGGCAGGATTTGGTTAGGATGGGTGGACGTTTGAAGTGA 403
Uce_Oryza_2         TGATCAAATTGTTAGCCACAACTTACTAAGCCTAAGGGAATCTTGCCACACTTTTTGAG 1366
UceA1.7             TTATTATTTTTT---ATTTTTTCTCTTTACTTTGTTTTTTTAGCTATTTCCAGCGACTAC 788
A-Tubulin_Coffea_2  TGTCTTGGTCCCCCATAATTGACTTCGGCTAAGTAAAGGAAAACCT--TAGCCGAGGCTG 640
35Sd_AMV            CACCTACAAATGCCATCATTGCGATAAAGGAAAGGCTATCGTTCAAGATGCCTCTGCCGA 430

Arabidopsis         TTATTTCTAATCCTTC----ATGGGTT--TTATGACGAA-TCGTGTGTTAGGGATTCGTTT 534
Uce_Oryza_3         TTATTTTTATGGGATA---TTCGCTT--TCGTGGCGG--CTGCGTTTCCTCG---CCCAT 275
Gos-2_Zea           TAGCACAGAAGGGACA---CTAGA--------AATGAC-TTGCTTGACTTAGAGTATCAG 349
Uce_Oryza_1         CACGGCAGTAACGCCC---TTTGCTGCTGTTAACGG--CCACCAACCCGCCGTGACGA 607
A-Tubulin_Coffea_1  TTGGTCAGGCCGGTAT---CCAGGTCGGAAATGCCTG--CTGGGAGCTCTACTGCCTCGA 1366
Uce_Oryza_4         TCACGTAGCGCAAATG---CCGCTCCCGTTTCCGCATC-GTGCGGATTTATCTCCTTTCTG 423
UBI9_Saccharum      ACTTGCAAGAGCGATG---TCAATGATGCCTGGAGTGT-ACAGGGTGGACCTCTTCACTC 793
Enolase_Zea         TAATTTTGGTTGGTTT---TTGCCTCGACTAGCTACCA--TTACCTCCTGCATCTAGACAT 464
Actin-2_Zea         TGAGTTTTTCAAGCGT---ATAGATTTTCTATTTGTCC-TTTTTAATTAACTTTCTCCCA 459
Uce_Oryza_2         CCATTGACACGTGGGA---GTGAATTTGTTAGAGGGAA-AT-CTTGCCACAACTGTGGCT 1421
UceA1.7             TAAACAAAATAAAAAT---TAGCCCAGGACAGGAGGAT-CTCTCAGCTACTTTTTCTCTC 844
A-Tubulin_Coffea_2  TAATTAAGCCGAAGTC---CTAACGCGATGGCGAACGG-CCGAGGTGGTCGGAGCCTAAG 696
35Sd_AMV            CAGTGGTCCCAAAGATGGACCCCCACCCACGAGGAGCA-TCGTGGAAAAAGAAGACGTTC 489

Arabidopsis         TTTCTGGGTTGGGTTTCTAAATTTGTTGGT-CTAAGAACAGTGAAAT-----TGTTGTTT 588
Uce_Oryza_3         ATATAAGAGCGGGTGACCACGACTGC--------GGCGCGCGCA---------CCACTC 318
Gos-2_Zea           ATA-AACATCATGTTTACTTAACTTTAAAT-TTGTATCGGTTTCTAC-----TATTTTTA 402
Uce_Oryza_1         A-ACGGCATCAGCTTTCCACCTCCTCGATA-TCTCCGCGGCGCCGTC-----TGGACCCG 660
A-Tubulin_Coffea_1  GCACGGCATCCAGGTAAATTGCCTTCTATC-TAACCTCTTATATTTC-----AGATCTGC 1420
Uce_Oryza_4         TTTCCGAATTTTATTAGTAGTTGCGATATTATTAATACAGGTCTCGT-----AGCGGCCG 483
UBI9_Saccharum      GTCAAGTGTCATCTCCTGACGTGGACTGGAGCTACGGTGAGCCAACCG-----AGATGTTA 849
Enolase_Zea         TACAAATTTACAATAAATAAAGTTCCTAGATTTTGAACGAAACCAGC-----AGAGCGCA 519
Actin-2_Zea         GCCGGGATGCGCGTATAAAAACCGGCGAAACCCTTGGCTCTCCTCATT----CGGCCTAT 515
Uce_Oryza_2         ACAACCAAACACCTGTCAAATTTGCCTAACCTTAGGCGTGGCAAACTG----TGGCAAAG 1477
UceA1.7             A---AAATTTCTCCAATTAGCTCTGTAATTTTCTATTTTGTTTCTCTT----TATTTTAG 897
A-Tubulin_Coffea_2  AGACATAGGCGGGACCCCAGCTCTGCCGACCTGGAAATACCCTCCTCA----TATACCAT 752
35Sd_AMV            CAACCACGTCTTCAAAGCAAGTGGATTGATGTGATATCTCCACTGACGTAAGGGATGACG 549
```

FIGURE 3E

```
Arabidopsis         CAGTGATC--CCAGATTCT-ACACTCT-AAATTTGTTGGTCTAA-GAA-----------C  632
Uce_Oryza_3         CACCACCA--CCA---CCA-CCACTCC-A--CCGATCGGCGAGA-GCG-----------C  357
Gos-2_Zea           TAATATTT--TTGTCTCTATAGATACT-ACGTGCAACAGTATAA-TCAA--------CCT  450
Uce_Oryza_1         CCCCCTTT--CCGTTCCTTTCTTTCCT-TCTCGCGTTTGCGTGG-TGGGGACGGACTCCC  716
A-Tubulin_Coffea_1  TGTTTCTC--TCATTTTTGTTCAAGGA-AATGATTCATCTTTGG-TTTGATTTTGGGTGT 1476
Uce_Oryza_4         CGTCTCCT--CCTCCCTTATATAAAGG-CAGCGTTTCTGCAAGT-TATTACCCAATCTAC  539
UBI9_Saccharum      TGCGCCGG--TTCCAATGATGGAGAGG-GGATGGGTGAGAGTGG-CGGAGCCTACATTGT  905
Enolase_Zea         CACCGTCC--TTG-CCCCACGGAACAA-GAAAAATGGAATATGC-TCCCGCAGCCCTCGT  574
Actin-2_Zea         CACAACCG--CTT-ACTCTCGTGCGCT-CTCCGTGGGAGCGAGG-ACCCGCGGCCG--GC  568
Uce_Oryza_2         TGTGGCTT--ACAACCAAACACACCCTTAGATAATAAAATGTGG-TCCAAAGCGTAATTC 1534
UceA1.7             ATTTTTTT--TGGTCCGTGTTAATCTTCGTTGAAGGCGATCTAGCTTTGATTTGAATTTC  955
A-Tubulin_Coffea_2  TACTAGTTAGTAGTCACCACTGCTACTGCTTCAGTTCCTTTTATCACTTGCTTTACATGA  812
35Sd_AMV            CACAATCCCACTATCCTTCGCAAGACCCTTCCTCTATATAAGGAAGTTCATTTCATTTGG  609

Arabidopsis         A-GTGAAATTGTTGTTTCAGT-GATCCCAG------------------------------  660
Uce_Oryza_3         G-GGGAGATCGTT-CGACGGC-GGCAAGATGC----------------------------  386
Gos-2_Zea           T-ATAATATTTTTGTCTCTATAGATACTACG-----------------------------  480
Uce_Oryza_1         C-AAACCGCCTCTCCCTCTCTTTATTTGTCTATATTCTCACTGGGCCCCACCCACCGCAC  775
A-Tubulin_Coffea_1  T-GTGGAATAGCCTGATGGACAAATGCCGAGCGACCACACCGTCGGAGGCGGAGACGACG 1535
Uce_Oryza_4         ACGAGAGAGAGATCGTTCGACGCATATAGAGAGAGAGAGAGAGATAGGGCAAGATGC----  594
UBI9_Saccharum      GCGCATACCGTGTGGGCCGCGGGATAAATACCTCAAGAAGGAAGCGTTGTGGCCTTACCT  965
Enolase_Zea         GGAAACCAAGGGCGGACCTTCCCCTC----------------------------------  600
Actin-2_Zea         GGCAGCGGCAGCTTCTCCTAGATCTCCGGCATCATCAGTGGATCC---------------  613
Uce_Oryza_2         ACTAAAAAAAAAT-CAACGAGACGTGTACCAAACGGAGAGCAACGGCATCTTCTCGAAAT 1593
UceA1.7             ATTTTTTTTCTTTTTCCTTTTAAGATACTTTTTTGTTTGTTTTAGGGTTTAGGCGATGG  1015
A-Tubulin_Coffea_2  ATTAAGTCGATGCTCTTCCTTAGAATAACTAGCGATTAGTTTCGTGGTGACCTATCTAGCC  872
35Sd_AMV            AGAGGAGATCTTTTTATTTTTAATTTTCTTTCAAATACTTCCAC----------------  653

Arabidopsis         ------------------------------------------------------------
Uce_Oryza_3         ------------------------------------------------------------
Gos-2_Zea           ------------------------------------------------------------
Uce_Oryza_1         CCCTGGGCCCACTCACGAGTCCCCCCCTCCCGACCT------------------------  811
A-Tubulin_Coffea_1  CTTTCAACACCTTCTTCAGCGAAACCGGAGCCGGCAAACACGTTCCTCGTGCCGTGTTCG 1595
Uce_Oryza_4         ------------------------------------------------------------
UBI9_Saccharum      CCAAGAGTTTGTCGATGGAGCCCTTGCGCATATCCTGAACATGTCCAAGGCTCTGGGAGA 1025
Enolase_Zea         ------------------------------------------------------------
Actin-2_Zea         ------------------------------------------------------------
Uce_Oryza_2         TTCCCAACCGCTGGCTGGCCCGCCTCGTCTTCCCGGAAACCGCGGTGGTTTCAGCGTGGC 1653
UceA1.7             CTTCAAAGCGGATCTTGAAGGAGCTCAAGGACCT-------------------------- 1049
A-Tubulin_Coffea_2  ATTTTTTCTGTTTGGGTGGCATCAATCCTGAACACAGAAAGCTGCAAG------------  919
35Sd_AMV            ------------------------------------------------------------

Arabidopsis         ------------------------------------------------------------
Uce_Oryza_3         ------------------------------------------------------------
Gos-2_Zea           ------------------------------------------------------------
Uce_Oryza_1         ------------------------------------------------------------
A-Tubulin_Coffea_1  TCGATCTGGAGCCCACTGTCATCGATGAAGTCCGAACCGGCACCTACCGCCAACTCTTCC 1655
Uce_Oryza_4         ------------------------------------------------------------
UBI9_Saccharum      GCAGGTTGGAAATGGGAGGCCAGTACTGCCTTACGTGATACATGGGCACTATGCC-----  1080
Enolase_Zea         ------------------------------------------------------------
Actin-2_Zea         ------------------------------------------------------------
Uce_Oryza_2         GGATTCTCCAAGCAGACGGAGACGTCACGGCACGGACTCCTCCCACCACCCAACCGCCA- 1712
UceA1.7             ------------------------------------------------------------
A-Tubulin_Coffea_2  ------------------------------------------------------------
35Sd_AMV            ------------------------------------------------------------

Arabidopsis         ------------------------------------------------------------
Uce_Oryza_3         ------------------------------------------------------------
Gos-2_Zea           ------------------------------------------------------------
Uce_Oryza_1         ------------------------------------------------------------
A-Tubulin_Coffea_1  ACCCTGAGCAGCTCAT-------------------------------------------- 1671
Uce_Oryza_4         ------------------------------------------------------------
UBI9_Saccharum      ------------------------------------------------------------
Enolase_Zea         ------------------------------------------------------------
Actin-2_Zea         ------------------------------------------------------------
Uce_Oryza_2         ------------------------------------------------------------
UceA1.7             ------------------------------------------------------------
A-Tubulin_Coffea_2  ------------------------------------------------------------
35Sd_AMV            ------------------------------------------------------------
```

FIGURE 3F

COMPOSITIONS AND METHODS FOR MODIFYING GENE EXPRESSION USING THE PROMOTER OF UBIQUITIN CONJUGATING PROTEIN CODING GENE OF COTTON PLANTS

CROSS-REFERENCES AND RELATED APPLICATIONS

This application claims priority to Brazilian patent application No. PI 0701230-6 filed in Brazil on Feb. 5, 2007. The disclosure of this earlier filed application is hereby incorporated herein by reference in its entirety and is hereby expressly made a portion of this application.

REFERENCE TO SEQUENCE LISTING, TABLE, OR COMPUTER PROGRAM LISTING

The present application is being filed along with a Sequence Listing in electronic format. The Sequence Listing is provided as a file entitled DSBIM1001AUSSEQ.TXT, created Dec. 21, 2010 which is about 16 KB in size. The information in the electronic format of the Sequence Listing is incorporated herein by reference in its entirety.

FIELD OF THE INVENTION

The present invention relates to a novel promoter for gene expression in plants. More specifically, the invention refers to regulatory sequences of polynucleotides isolated from cotton plants capable of initiating and activating the transcription of polynucleotides, and the use of these regulatory sequences for modifying the transcription of endogenous and/or heterologous polynucleotides and the production of polypeptides. The invention also describes DNA constructs that contain the promoter of ubiquitin conjugating protein coding gene of cotton plants operably linked to a heterologous and/or endogenous gene. Furthermore, the invention concerns the use of these constructs in the form of expression vectors, recombinant vectors and in plants, plant cells or transgenic protoplasts. The invention also describes a method using such constructs containing the promoter of ubiquitin conjugating protein coding gene of cotton plants for the production of plants, plant cells or transgenic protoplasts.

BACKGROUND OF THE INVENTION

The expression of a gene is regulated, at least partly, by cellular processes involved in transcription. During transcription, a single strand RNA, complementary to DNA, sequence is formed by the action of RNA polymerases. The start of transcription in eukaryotic cells is regulated by complex interaction between cis-active DNA motives located within the gene to be transcribed and trans-active protein factors. Among cis-active regulatory regions are the DNA sequences known as promoters, to which RNA polymerase primarily binds, directly or indirectly. For the purpose of the present invention, the term "promoter" refers to the specific DNA sequences—usually "upstream" (5') of the coding region of a structural gene—that controls the expression of this coding region due to its ability to provide a recognition site for the RNA polymerase and/or other necessary factors for initiating transcription, as well as defining the correct location for gene transcription.

Typically, a promoter sequence comprises a "TATA box" and an upstream activating region. This TATA box is responsible for defining the location of transcription start site, normally approximately 25 base pairs towards the start of the coding sequence of the gene (3').

These promoters are basically divided into inducible and non-inducible (also termed constitutive) types. An inducible promoter is one capable of activating (directly or indirectly) the transcription of one or more DNA sequences or genes in response to a determined inducer. When there is no inducer, the DNA sequences or genes are not transcribed. This inducer may be a chemical component (described in patent document WO9519443, for example), some form of stress of physiological origin (such as in the case of wounds, described in patent document U.S. Pat. No. 6,677,505, for example), or an endogenous compound generated in response to changes in plant development.

There are many tissue-specific promoters described in plants, such as the case of specific expression in seed (WO8903887), tubercle (as mentioned in patent application US20030175783, Keil et al., 1989 EMBO J. 8: 1323:1330), leaves (as mentioned in patent application US20030175783, Hudspeth et al., 1989 Plant Mol. Biol. 12:579-589), fruit (Edwards & Coruzzi (1990) Annu. Rev. Genet. 24, 275 to 303 and U.S. Pat. No. 5,753,475), stem (as mentioned in patent application US20030175783, Keller et al., 1988 EMBO J. 7: 3625-3633), vascular tissue (as mentioned in patent application US20030175783, Peleman et al., 1989 Gene 84: 359-369 and Schmülling et al. (1989) Plant Cell 1, 665-670), root (US20060143735 as mentioned in patent application US20030175783, Keller et al., 1989 Genes Devel. 3:1639-1646), stamen (WO8910396, WO9213956), specific promoters for the dehiscence zone (WO9713865) and meristem (Ito et al. (1994) Plant Molecular Biology, 24, 863 to 878).

On the other hand, constitutive promoters are capable of conducting the expression of DNA sequences throughout the development of a plant and lack specificity as to the site of sequence expression. Therefore, expression occurs in a large variety of cells and tissues of the plant. Despite this, the term "constitutive" does not imply that the sequence is expressed in similar levels in all plant cells.

Recombination techniques make it possible to trigger the transcription start site of a nucleotide sequence of interest—such as a heterologous or non-natural sequence—in a plant host cell.

The promoters that drive constitutive expression of the genes under their control may be used, for example, to select transformed plant cells, to express a selection marker gene in transgenic plants, in generating plant cells resistant to antibiotics or for creating herbicide or insecticide tolerant plants and pathogen stress resistant plants, since the products of the genes controlled by these promoters are present in all parts of the plant.

Exogenous genes of agronomic, medical or other interest may be expressed in a variety of plants, for example, to generate heterologous recombinant proteins and for the generation of plants that contain mammal polypeptides. The quantities of expression patterns—both in terms of time and space—of endogenous plant genes may also be advantageously altered with the help of constitutively active promoters.

The first promoters used for the expression of genes in plants were of viral or bacterial origin, for example, bacteria from *Agrobacterium* genus. Both viral and bacterial systems carry advantages in the case of heterologous expression in plants since this character constitutes the basis of their infection mechanisms. Many of these promoters have being widely used for expressing proteins of interest in the production of genetically modified plants.

Apart from *Agrobacterium* T-DNA derived promoters, such as those responsible for synthase of manopine (mas), octopine (ocs) and nopaline (nos), there are also virus derived promoters, with the most commonly used being CaMV35S, which corresponds to the cauliflower mosaic virus 35S promoter fragment. Later, this same promoter had its regulatory region duplicated and fused to an enhancer sequence of the alfalfa mosaic virus, generating a highly efficient recombinant plant promoter for inducing expression of coding sequences associated to it.

Other constitutive promoters of viral origin are, for example, the scrofularia mosaic virus promoter (PI1101063-0), of the badnavirus that infects the Australian banana (U.S. Pat. No. 6,391,639) and the promoter of the sugar-cane baciliform virus (U.S. Pat. No. 6,489,462). However, viral and *Agrobacterium* promoters present problems related to their regulatory capacity and may be particularly unstable and suitable to horizontal gene transfer and gene recombination, which tends to highlight the importance of seeking promoters of plant origin.

Typical constitutive promoters of plants are, for example, the coffee alpha tubulin promoter (U.S. Pat. No. 6,441,273), the *A. thaliana* trehalose 6-phosphate synthase protein promoter (US20020115850), maize actin-2, enolase, Gos-2 and L41 promoters (U.S. Pat. No. 6,670,467), *Beta vulgaris* V-ATPase promoter (PI0013537-2), *Brassica* hsp80 promoter (PI9300296-3).

Despite that many of these plant promoters demonstrate a strong expression, data for the promoters presented herein basically refers to a qualitative analysis. However, the present invention further presents quantitative data obtained by means of fluorimetric tests that upon analysis demonstrated its high expression capacity.

The promoters described above were aligned with the present invention and showed no significant sequence identity between them. The coffee alpha tubulin promoter obtained the best alignment with an identity of 44.3%. This alignment may be performed using softwares available on the internet, with one being the BLASTN provided on the National Centre for Biotechnology Information/NCBI page: (ncbi.nlm.nih.gov.

The *A. thaliana* trehalose 6-phosphate synthase protein promoter (US20020115850) shows a reduction in activity in root during plant development. The present invention, however, presents high expression throughout plant tissues of transgenic *Arabidopsis* over 3 months, showing that uceA1.7 presents expression capacity in high levels, not only during development stages but also in mature plants, which constitutes great technological potential considering that most plants are attacked by insect-pests throughout plant's life.

It is desirable that whenever possible the available promoters enabling expression of selection genes and resistance genes present strong and uniform constitutive activity, when possible, throughout plant tissues or cell types that, furthermore, present even greater activity or are not inhibited under stress conditions.

Even if the above mentioned promoters are considered as being constitutive, time and spatial expression patterns are different rendering them inappropriate for determined purposes. This makes the search and study for other plant promoters crucial. Furthermore, high expression levels are needed to increase the levels of the protein product of interest required for certain purposes in the generation of genetically modified plants. High protein expression levels help in the generation of plants by presenting commercially important phenotype properties, such as resistance to insect-pests and diseases, environmental stress tolerance (e.g. drought, high temperatures, cold, light intensity, photoperiod and chemicals, amongst others), improved quality (e.g. high fruit yield, extended life cycle, size and color uniformity, high sugar content, high vitamin A and C and reduced acidity, amongst others).

Promoters may become more effective when isolated from the same species of the transgenic plant generated. The expression of β-glucuronidase (GUS) controlled by rice actin (Act1) promoter in protoplasts of transformed rice was approximately 6 times greater than the expression controlled by the maize constitutive promoter alcohol dehydrogenase (Adh1) (U.S. Pat. No. 658,701). Therefore, apart from being used as constitutive promoters for various plant species, the present invention advances a promoter having great advantages concerning the production of transgenic cotton plants.

Ubiquitin is one of the more conserved proteins in eukaryotes. One of the physiological functions of ubiquitin is to conjugate with a target protein as a recognition signal for protein degradation. Selective degradation of abnormal proteins is performed on many short lived regulatory proteins, including cell cycle proteins, cellular growth modulators and transcription factors. In more complex organisms, ubiquitin has been encoded by two small gene families termed "polyubiquitin genes" and "ubiquitin fusion genes". Polyubiquitin genes comprise a tandem repetition of 228 bp head to tail, with each repetition encoding 76 amino acids of an ubiquitin monomer. The number of tandem repetitions indicated variations in the genes within the genomes and between organisms, ranging from 3 in *Dictostylium* to approximately 50 in *Trypanosoma cruzi*. On the other hand, the ubiquitin fusion gene family encodes a simple repetition fused with one or two polypeptides having 52 or 76-80 amino acids each (Callis et al., "Ubiquitin and Ubiquitin Genes in Higher Plants", Oxford Surveys of Plant Molecular & Cell Biology, (1989), vol. 6, pp. 1-30). Studies of ubiquitin genes in different plants show that ubiquitin genes are expressed in all tissues; however, the differential expression of ubiquitin genes can also be observed in the ubiquitin gene family. Each tandem repetition or ubiquitin gene may be differentially expressed in cells or tissues.

Ubiquitin gene promoters have demonstrated the ability to conduct the expression of genes—usually GUS or chloramphenicol acetyltransferase (CAT)—in transformed cells or plants. Such promoters have been isolated from *Arabidopsis* (Callis et al., "Ubiquitin Extension Proteins of *A. thaliana*", The Journal of Biological Chemistry (1990), vol. 265, n. 21, pp. 12486-12493); sunflower (Binet et al., "Analysis of a sunflower polyubiquitin promoter by transient expression" (1991) Plant Science, vol 79, pp. 87-94); tobacco (Genschick et al., "Structure and promoter activity of a stress and developmentally regulated polyubiquitin encoding gene of *Nicotiana tabacum*", Gene, (1994) vol. 148, pp. 195-202); maize (US20030066108; U.S. Pat. No. 6,020,190; U.S. Pat. No. 5,614,399; U.S. Pat. No. 5,510,474; Christensen et al., "Maize polyubiquitin genes: structure, thermal perturbation of expression and transcript splicing, and promoter activity following transfer to protoplasts by electroporation", Plant Molecular Biology, (1992) vol. 18, pp. 675-689); rice (U.S. Pat. No. 6,528,701); sugar-cane (U.S. Pat. No. 6,706,948); celery (WO2003102198); Pine and eucalyptus (PI0309870-2). These promoters were aligned with the present invention using BLASTN and showed no similarity. Patent documents US20030066108; U.S. Pat. No. 6,020,190; U.S. Pat. No. 5,614,399 and U.S. Pat. No. 5,510,474 describe engineered versions of the maize ubiquitin promoter used to increase expression levels compared to the expression levels of the native ubiquitin promoter. The invention reports that the promoter regulates the expression of maize polyubiquitin gene containing 7 tandem repetitions. The expression of this ubiquitin gene proved constitutive at 25° C. and was heat induced at 42° C. This promoter was used successfully to transform monocots other than maize, including wheat, barley and rice. However, the promoter of the present invention proved to be an excellent constitutive promoter and does not undergo any change in expression levels when submitted to different temperatures as well as presenting high expression throughout the plant cycle.

Cotton (*Gossypium* spp) is one of the most important cultures in the world, and is considered to be the most important of all textile fibres. Brazil holds a prominent position amongst the world's main cotton producers. However, the increase of production costs is influenced by agricultural problems, such as insect pest control, which represents approximately 25% of total production costs.

The production of genetically modified plants expressing proteins conferring resistance to the plant has been used with great success in insect-pests control. However, it is necessary to control and target the expression of these entomotoxic proteins in order to obtain these plants. The choice of the promoters that conduct expression is very important for obtaining transgenic plants affording adequate protein levels conferring insect resistance to plants. However, there are few effective promoters for expressing cotton plants available on the market at present, and none that demonstrate superior expression efficiency compared to the promoter of the present invention.

SUMMARY OF THE INVENTION

The present invention relates to a description of a novel regulatory sequence provided to improve the expression of a nucleotide sequence, such as structural genes, in plants, including monocots and dicots. In accordance with the present invention, a constitutive promoter for cotton plants (*Gossypium hirsutum*) termed uceA1.7 is described together with a method for the use of this regulatory polynucleotide region for the modification of endogenous and/or heterologous polynucleotide expression in transgenic plants.

In a first embodiment, the present invention provides a polynucleotide sequence isolated from cotton plants (*G. hirsutum*) comprising at least about 40 or 45%, 50 or 55%, 60 or 65%, 70 or 75%, 80 or 85%, 90%, 91%, 92%, 93%, 94%, 95%, 96%, 97%, 98%, or 99%, when compared with SEQ ID NO:1, wherein said polynucleotide has constitutive promoter activity. Additionally, the present invention provides sequences that are the complement of said polynucleotide sequence; the reverse complement of said polynucleotide sequence; the reverse of said polynucleotide sequence; and probes and primers corresponding to SEQ ID NO:1.

In another embodiment, the present invention provides chimeric genes comprising sequences having sequence identity at least about 40 or 45%, 50 or 55%, 60 or 65%, 70 or 75%, 80 or 85%, 90%, 91%, 92%, 93%, 94%, 95%, 96%, 97%, 98%, or 99%, when compared with SEQ ID NO:1, optionally linked to expression enhancer or promoter sequences of interest; operably linked to a polynucleotide sequences of interest. In addition, cells and organisms may comprise said chimeric genes.

In a related embodiment, the present invention provides recombinant vectors incorporating a promoter sequence in 5'-3' sense for the polynucleotide of the present invention, a polynucleotide to be transcribed and a gene termination sequence. A recombinant vector may comprise a sequence having sequence identity at least about 40 or 45%, 50 or 55%, 60 or 65%, 70 or 75%, 80 or 85%, 90%, 91%, 92%, 93%, 94%, 95%, 96%, 97%, 98%, or 99%, when compared with SEQ ID NO:1, optionally linked to an expression enhancer or promoter sequences of interest; operably linked to a polynucleotide sequence of interest; and a termination sequence. The polynucleotide to be transcribed may either incorporate the open reading frame of a polynucleotide encoding a polypeptide of interest, or may be a non-translated, or non-encoding region of a polynucleotide of interest. The open reading frame may be oriented in "sense" or "antisense" direction. Preferably, the gene termination sequence is functional in a host plant. More preferably, the gene terminator sequence is that of the gene of interest, but may be others described in the state of the art (see Benjamin Lewin, Genes VIII, chapter 9) such as nopaline synthase terminator of *A. tumefasciens*. The recombinant vectors may also include a marker for identifying the transformed cells.

In yet another embodiment, cells of transgenic plants comprising the recombinant vector of the present invention are provided, together with organisms, such as plants, incorporating these transgenic cells, and the fruits, seeds and other products, derivates, or progeny of these plants. The propagula of the inventive transgenic plants are included in the present invention.

Another embodiment of the present invention provides a method for modifying the expression of genes in an organism, such as a plant, including stable incorporation in the genome of the organism containing the recombinant vector of the present invention.

A further embodiment of the present invention provides a method for producing a transformed organism, such as a plant, through the expression of a modified polypeptide. This method consists in transforming a plant cell with the recombinant vector of the present invention in order to provide a transgenic cell under conditions conducive to the regeneration and growth of the mature plant.

Yet another embodiment of the present invention provides a method for identifying a gene responsible for a certain function or desired phenotype. The method comprises: 1) transformation of a plant cell containing a recombinant vector comprising a polynucleotide promoter sequence of the present invention operationally linked to a polynucleotide to be tested, 2) plant cell culture under conditions capable of inducting regeneration and growth of mature plant in a manner as to produce a transgenic plant, and, 3) comparing transgenic plants phenotype with those of non-transformed plants, or of wild plants.

All the above mentioned embodiments and others of the present invention as well as the means of obtaining these shall be made evident and the invention may be better understood referring to the "Detailed Description of the Invention".

BRIEF DESCRIPTION OF THE FIGURES

FIGS. 3A-3F—Alignment between the different constitutive plant promoters and the promoter of the present invention (uceA1.7). Sequences include the following: *Arabidopsis* (SEQ ID NO:07); Uce_Oryza_3 (SEQ ID NO:08); Gos-2_Zea (SEQ ID NO:09); Uce_Oryza_1 (SEQ ID NO:10);

A-Tubulin_Coffea_1 (SEQ ID NO:11); Uce_Oryza_4 (SEQ ID NO:12); UBI9_Saccharum (SEQ ID NO:13); Enolase_Zea (SEQ ID NO:14); Actin-2_Zea (SEQ ID NO:15); Uce_Oryza_2 (SEQ ID NO:16); UceA1.7 (SEQ ID NO:01); A-Tubulin_Coffea_2 (SEQ ID NO:17); and 35Sd_AMV (SEQ ID NO:18).

Figure 4:
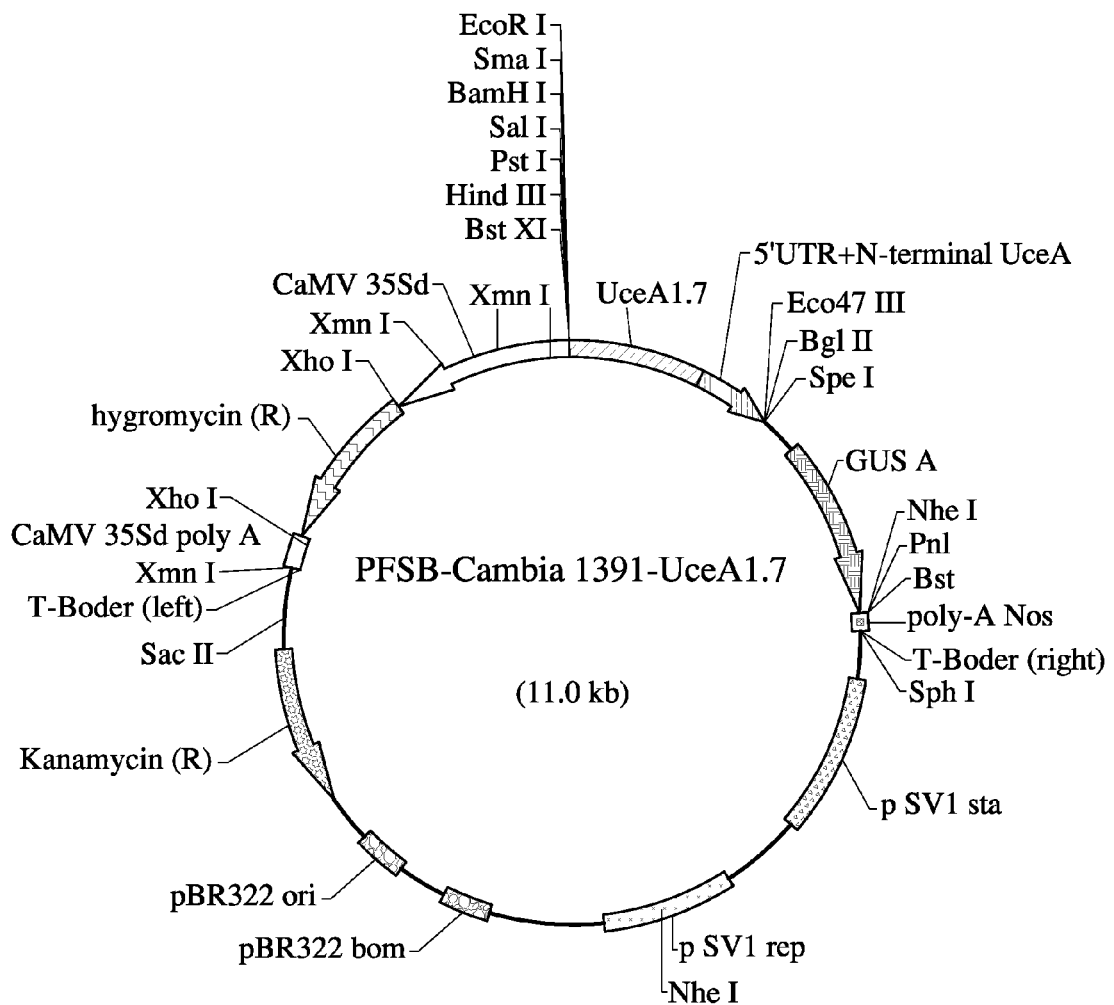

FIG. 4—pCAMBIA1391 vector linked to 1.0 kb insert. The figure shows a schematic representation of the pCAMBIA1391, (a) containing the double 35S promoter with the AMV (Alfalfa Mosaic Virus) enhancer together with gusA gene, as a positive control, and (b) containing cotton uceA1.7 promoter (SEQ ID NO:1) of 1.0 kb, together with gusA gene for *A. thaliana* plants transformation.

Figure 5:
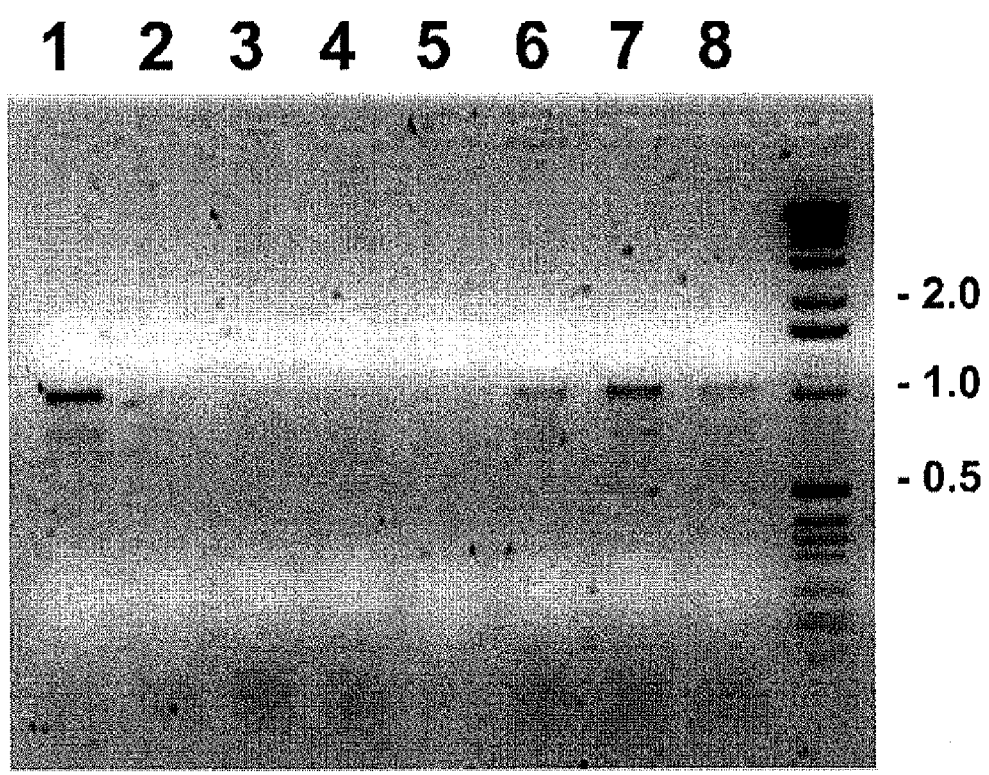

FIG. 5—Agarose gel image showing the cotton promoter (clone uceA1) subcloning in pCAMBIA1391. The numbers indicate the number of clones analysed. Clones 1, 6, 7 and 8 are positive. The molecular mass marker (1.0 kb DNA-ladder, Gibco-BRL) is indicated in kb.

Figure 6:
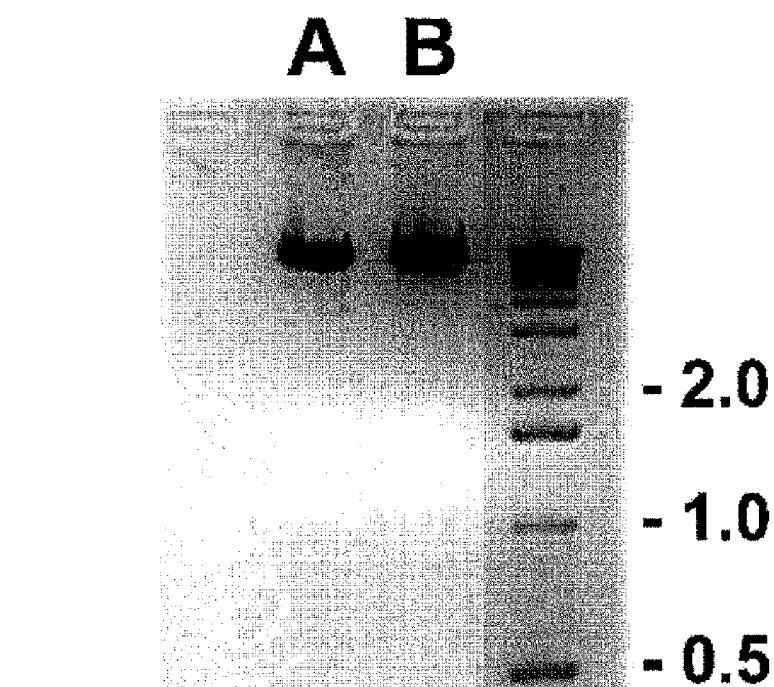

FIG. 6—Agarose gel image of clones uceA1.1 and uceA1.7 digested with Hind III and Xba I, for analysis of the cotton promoter direction (clone uceA1) subcloned to vector pCAMBIA1391. (A) clone uceA1.1; (B) clone uceA1.7. The arrow indicates the intended fragment of approximately 200 bp obtained in the digestion for the clones in a sense orientation. Both clones have the promoter in a correct (sense) orientation in relation to gene gusA present in the vector. Clone uceA1.7 was selected for further manipulation. The molecular mass marker (1.0 kb DNA-ladder, Gibco-BRL) is indicated in kb.

Figure 7:
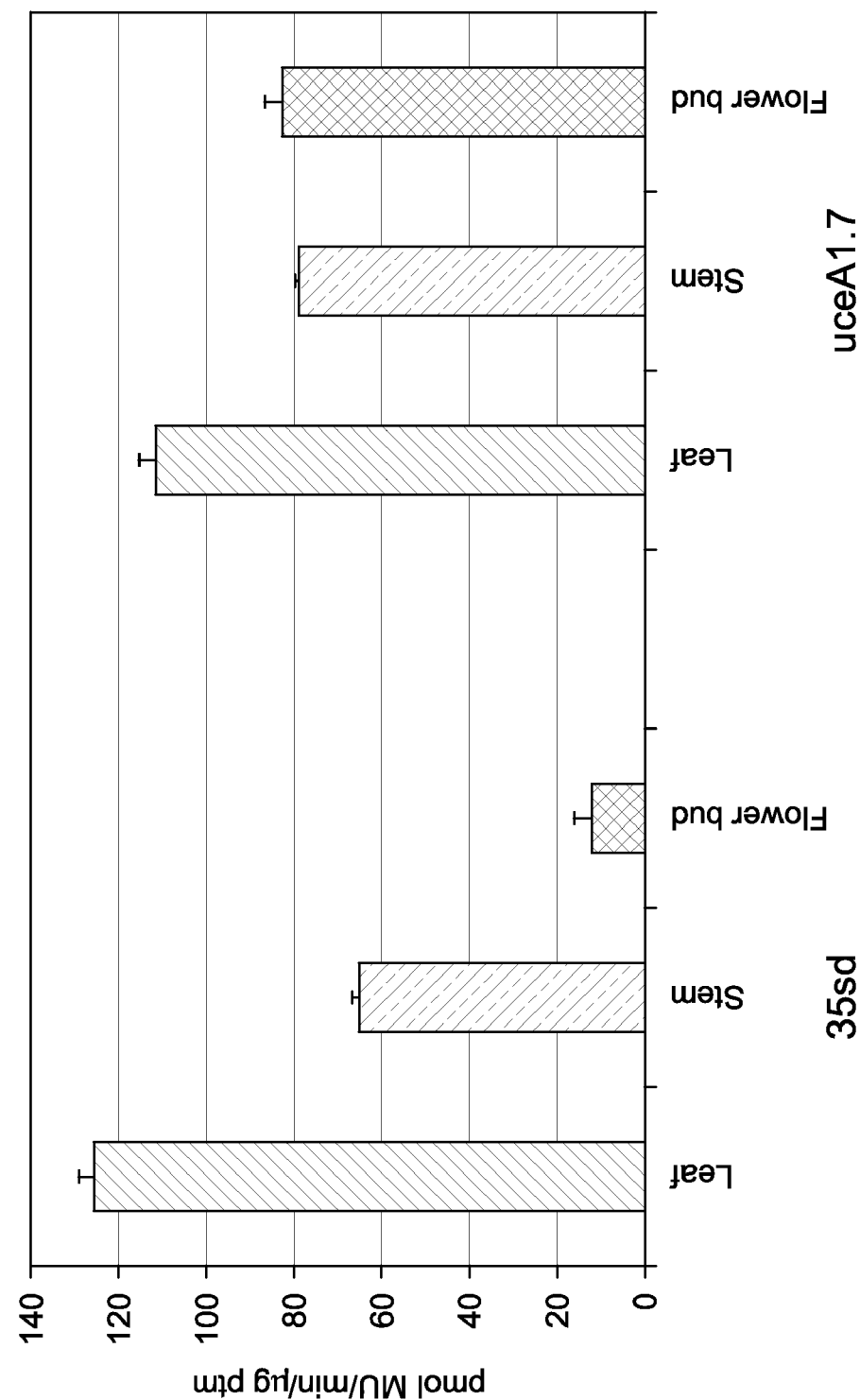

FIG. 7—Fluorimetric test of specific GUS activity in different parts of the *A. thaliana* plant (leaves, stem, flower bud) conducted by d35S and uceA1.7 promoters.

Figure 8:
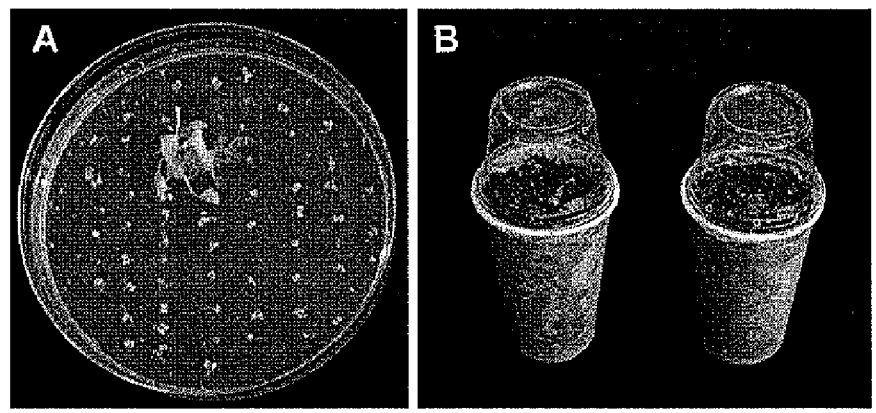

FIG. 8 *A. thaliana*—Columbia seeds and plants transformed with a vector containing the promoter sequence SEQ ID NO:1. Panel A shows seeds sown in MS culture medium with 20 μg/ml hygromycin to select for transformants containing pCAMBIA1391 vector with the sequence SEQ ID NO:1. Panel B shows germinating and rooted plantlets derived from transformed seeds in cups containing sterile soil and covered so as to retain humidity.

Figure 9:
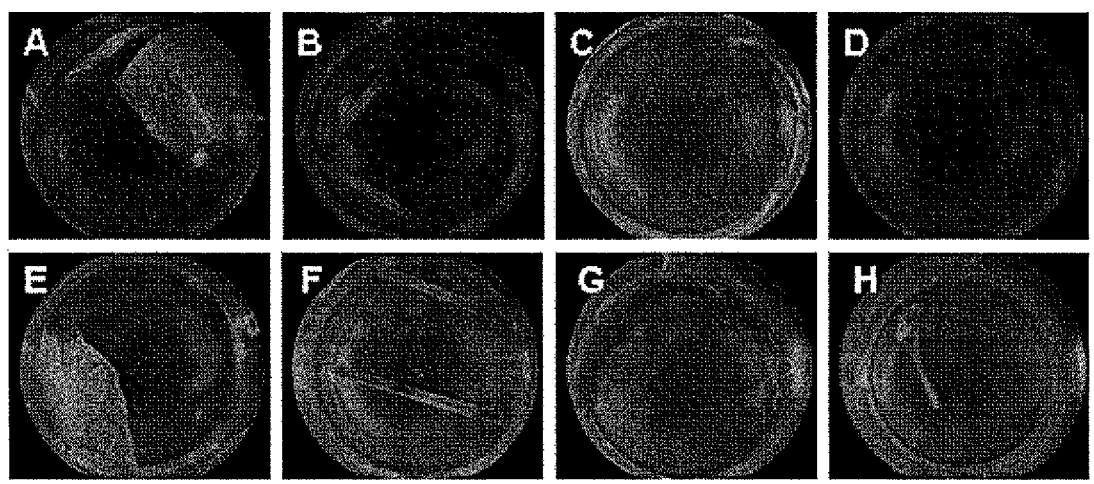

FIG. 9—A X-gluc assay showing β-glucuronidase expression from cuts of transformed *A. thaliana* plants. Panels A-D show gus gene expression in cuts taken from (A) leaves, (B) stem, (C) roots, and (D) floral buds of plants transformed with a vector containing the double CaMV35S (Cauliflower Mosaic Virus 35S promoter) with the sequence enhancer of the AMV (Alfalfa Mosaic Virus) (CaMV35SdAMV). Panels E-H show gus gene expression in cuts taken from gus gene expression in cuts taken from (E) leaves, (F) stem, (G) roots, and (H) floral buds of plants transformed with a vector containing a sense construction of the uceA1.7 cotton promoter with CaMV35SdAMV.

DETAILED DESCRIPTION OF THE INVENTION

In the context of this description, several terms are used and it therefore seems appropriate to provide the following definitions for these:

The term "chimeric gene" refers to a gene incorporating a promoter and an encoding region having different origins. In the case of the present invention, the chimeric gene includes the polynucleotide of the present invention linking the encoding regions of endogenous and/or exogenous genes.

The term "consensus sequence" refers to an artificial sequence in which the base of each position represents the base more frequently found in the actual sequence when comparing to different alleles, genes or organisms sequences.

The term "promoter" refers to a DNA portion that is upstream to the coding region and contains RNA polymerase II binding sites to initiate the DNA transcription.

The term "expression" refers to the transcription or translation of a structural, endogenous or heterologous gene.

The term "GC box" refers to a common element in the promoter that may increase promoter activity.

The term "TATA box" refers to a promoter element, located approximately 30 bases upstream the transcription initiation site. The TATA box is associated to transcription factors in general, including RNA polymerase II.

The term "gene" refers to a physical and functional heredity unit represented by a DNA segment that encodes a functional protein or RNA molecule.

The term "endogenous gene" refers to a gene specific to the cell or organism.

The term "heterologous gene" refers to a gene isolated from a donor organism and recombined in the transformed host organism. It is a gene that is not specific to the cell or organism.

The term "reporter gene" refers to an encoding unit having a readily tested product, for example, CAT, GUS, GAL, LUC and GFP genes. Expression of a reporter gene may be used to test the function of a promoter linked to this reporter gene.

The term "propagulum" as used in the present invention refers to any part of a plant that may be used for the reproduction or propagation, whether sexual or asexual, including plant cuttings.

The term "sense" means that the sequence of the polynucleotide is in the same 5'-3' orientation in relation to the promoter.

The term "antisense" means that the sequence of the polynucleotide is in the opposite orientation in relation to the 5'-3' promoter direction.

The term "x-mer"—when used as a reference for the specific value of "x" herein—refers to a sequence incorporating at least a specific number ("x") of polynucleotide residues identified as SEQ ID NO:1. In accordance with the preferred embodiments, the value of x is preferably at least 20, more preferably at least 40, even more preferably at least 60 and most preferably at least 80. Thus, the polynucleotide of the present invention include a polynucleotide of 20 mer, 40 mer, 60 mer, 80 mer, 100 mer, 120 mer, 150 mer, 180 mer, 220 mer, 250 mer, 300 mer, 400 mer, 500 mer or 600 mer identified as SEQ ID NO:1 and variants thereof.

The term "polynucleotide(s)" refers to a single or double strand polymer with deoxyribonucleotide or ribonucleotide bases and includes corresponding RNA and DNA molecules, including HnRNA and mRNA molecules, both sense and antisense strands, and incorporates cDNA, genomic DNA and recombinant DNA, as well as completely or partially synthesised polynucleotides. A HnRNA molecule contains introns and corresponds to a DNA molecule generally in a one to one mode. A mRNA molecule corresponds to a DNA and HnRNA molecule from which all introns were excised. A polynucleotide may consist of a complete gene, or any portion thereof. The operational antisense polynucleotides may incorporate a fragment of the corresponding polynucleotide, and the definition for "polynucleotide" thus includes all of these operational antisense fragments. The antisense polynucleotides and techniques involving antisense polynucleotides are well known in the state of the art. (J. Sambrook; E. F. Fritsh and T. Maniatis-Molecular cloning. A laboratory manual, $2^{nd}$ Ed., Cold Spring Harbor Laboratory Press, 1989.).

The polynucleotides described in the present invention are preferably approximately 80% pure, more preferably 90% pure, and most preferably at least 99% pure.

The term "oligonculeotide" refers to a relatively short segment of a polynucleotide sequence, generally incorporating between 6 and 60 nucleotides. These oligonucleotides may be used as probes or primers, whereby the probes may be used to serve as hybridisation tests and primers are used in DNA amplification by PCR.

The term "probe" used in the present invention refers to an oligonucleotide, polynucleotide or nucleic acid, being RNA or DNA, occurring naturally such as a purified product of restriction enzyme digestion or being synthetically produced, capable of specifically annealing or hybridising with a nucleic acid containing complementary sequences to the probe. A probe may also be single chain or double chain. The exact length of the probe will depend on many factors, including temperature, probe origin and use of the method. For example, an oligonucleotide probe will typically contain between 15-25 or more nucleotides depending on the complexity of the target sequence, although it may contain fewer nucleotides. The probes herein are selected in order to complement the different chains of a particular nucleic acid sequence. This means that a probe may be sufficiently complementary to be able to "hybridise specifically" or for annealing with their respective target chains under a series of pre-determined conditions. Consequently, the probe sequence does not necessarily exactly reflect the complementary target sequence. For example, a fragment of non-complementary nucleotide may be linked to the 5' or 3' end of the probe, with the remaining probe sequence being complementary to the target chain. Alternatively, non-complementary bases or long sequences may be interspersed within the probe if it is sufficiently complementary with the sequence of the target nucleic acid to specifically anneal with it.

The term "primer" refers to an oligonucleotide, being RNA or DNA, single chain or double chain, derived from a biological system, generated by digestion with restriction enzymes or being synthetically produced, that, when placed in an appropriate environment, is capable of acting functionally as the primer for the synthesis of nucleic acid depending on the template. When in presence of an appropriate nucleic acid template, adequate nucleoside triphosphate precursors of nucleic acids, a polymerase enzyme, adequate cofactors and suitable conditions such as adequate temperatures and pH values, the primer may be extended at its 3' terminal through the addition of nucleotides by polymerase activity or some similar activity to produce a first extension of the product. The primer may vary in length depending on particular conditions and requirements for use. For example, when used as a diagnostic, the oligonucleotide 'primer' typically has a length of 15-25 or more nucleotides. The 'primer' must have sufficient complementarity with the intended template to initiate extension synthesis of the product. This does not mean that the 'primer' sequence must precisely complement the intended template. For example, a non-complementary nucleotide sequence may be linked to the 5'terminal of a complementary 'primer'. Alternatively, non-complementary bases may be interspersed within the oligonucleotide sequence of the 'primer', provided the 'primer' has sufficient complementarity with the desired template chain sequence to functionally form a template-primer complex for the extension synthesis of the product.

The term "specifically hybridise" refers to the association of two single chain nucleic acid molecules having sufficiently complementary sequences in order to allow such hybridization under pre-determined conditions commonly described in the state of the art (Handbook: Tecnologia de DNA recombinant. Universidade de São Paulo, Chapter 1, 2003) [Recombinant DNA technology. University of São Paulo].

More precisely, the term refers to the hybridisation of an oligonucleotide with a substantially complementary sequence containing a single chain RNA molecule or DNA molecule from the present invention. Optimal conditions necessary for specific hybridisation between single chain nucleic acid molecules of varying complementarity are well described in the state-of-the-art (Handbook: Tecnologia de DNA recombinant. Universidade de São Paulo, Chapter 4, 2003) [Recombinant DNA technology. University of São Paulo]. A common formula enabling calculation of the required stringency conditions to obtain hybridization between nucleic acid molecules is provided below (Sambrook et al., Molecular Cloning, A Laboratory Manual, $2^{nd}$ Ed. (1989), Cold Spring Harbor Laboratory Press):

$$T_m = 81.5° C. + 16.6 \, \text{Log} \, [Na+] + 0.41(\% \, G+C) - 0.63(\% \, \text{formamide}) - 600/\text{bp in duplex (probe)}$$

As can be seen from the above formula, using $[Na+]=[0.368]$ and 50% of formamide, with 42% GC content and an average probe size of 200 bases, $T_m$ shall be 57° C.

Probes or primers are described as corresponding to the polynucleotide of the present invention identified as SEQ ID NO:1 or a variant thereof, when the oligonucleotide probe or primer, or its complement, are contained within the sequence specified as SEQ ID NO:11 or a variant thereof.

The term "oligonucleotide" refers to 'primers' and 'probes' of the present invention, and it is defined as a molecule of nucleic acid incorporating two or more ribo- or deoxyribonucleotides, preferably more than three. The exact size of the oligonucleotides depends on various factors and in the particular purpose and use of the oligonucleotide. Preferred oligonucleotides incorporate 15-50 consecutive complementary base pairs for SEQ ID NO:1. The probes may be easily selected using procedures thoroughly described in the state of the art (Sambrook et al., Molecular Cloning, A Laboratory Manual, $2^{nd}$ Ed. (1989), Cold Spring Harbor Laboratory Press, NY), taking into consideration DNA-DNA hybridization stringency, recombination and melting temperatures ($T_m$), as well as the potential for forming bonds and other factors, all well known in the state of the art.

The terms "complement", "reverse complement" and "reverse sequence" referred to herein are described in the following example: For sequence 5'AGTGAAGT3', the complement is 3'TCACTTCA5', the reverse complement is 3'ACTTCACT5' and the reverse sequence is 5'TGAAGTGA3'.

The term "variant" or "substantially similar" refers to different sequences of amino acids or nucleotides with specifically identified sequences, in which one or more nucleotides or amino acid residues are deleted, substituted or added. The variants may be naturally occurring allelic variants or non-naturally occurring variants. The variant or substantially similar sequences refer to fragments of nucleic acid that may be characterised by the percentage of similarity in their nucleotide sequences with the nucleotide sequences described herein (SEQ ID NO:1), determined by common algorithms used in the state of the art. The preferred fragments of nucleic acid are those whose nucleotide sequence has a sequence identity of around 40 or 45% at least, preferably a sequence identity of around 50 or 55%, more preferably a sequence identity of around 60 or 65%, more preferably a sequence identity of around 70 or 75%, more preferably a sequence identity of around 80 or 85%, and even more preferably a sequence identity of around 90%, 91%, 92%, 93%, 94%, 95%, 96%, 97%, 98% or 99%, when compared to the reference sequence. The percentage identity is determined by aligning the two sequences to be compared, determining the number of identical residues in the aligned portion, dividing this number by the total number of residues in the sequence under study and multiplying the result by 100. This alignment may be performed using software available on the internet, with one being the BLASTN provided on the National Centre for Biotechnology Information/NCBI page: (ncbi.nlm.nih.gov).

The term "vector" refers to a replicon, such as a plasmid, cosmid, bacamid, phagus or virus, to which other genetic sequences or elements (whether DNA or RNA) may be linked to be replicated together with the vector. Preferably, the virus derived vector is selected from bacteriophage, vaccinia virus, retrovirus or bovine pappilomavirus. A "recombinant vector" is result of combination of a commercial vector with chimeric genes, or the polynucleotide of the present operably linked to an endogenous and/or heterologous polynucleotide of interest that in turn is operably linked to a termination signal sequence. Such vectors may be obtained commercially, and include Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.). Some examples of vectors used in the present invention but not limited to these—are the pGEM-T and pCAMBIA1391.

The term "expression enhancer sequences" refers to amplifiers—or "enhancers" as they are more commonly known—that may be located very far from the promoter (either "upstream" or "downstream") and intensify the transcription of any nearby promoter. The gene expression efficiency in a specific tissue depends on the appropriate combination and integration of the enhancers, the promoters and the adjacent sequences.

The first enhancer that stimulated the transcription of eukaryote genes to be discovered was SV40 (present in the Simian Virus 40 genome). Hundreds of other enhancers were discovered in other viral genomes in eukaryote cells DNA following the discovery of the SV40 enhancer, such as HSV-1, AMV, HPV-16. (Lodish et al., Biologia celular e molecular. [Molecular and cellular biology]$4^{th}$ Ed. p. 368).

The term "operably linked" means that regulatory sequences necessary for the expression of the encoding sequence are placed in the DNA molecule in appropriate positions in relation to the coding sequence enabling the expression of the coding sequence. This same definition is sometimes applied to the arrangement of encoding sequences and elements controlling the transcription (such as, for example, promoters, "enhancers" and elements or termination sequences) in the expression vector. An exogenous coding region is typically flanked by operably linked regulatory regions that regulate the expression of the exogenous coding region in a transformed cell (which may be a micro-organism, plant or animal). A typical regulatory region operably linked to an exogenous coding region includes a promoter, inasmuch, a nucleic acid fragment that may cause the transcription of exogenous coding regions, positioned in 5' of the exogenous coding region. In the case of the present invention, the regulatory region refers to regions substantially similar to SEQ ID NO:1. To help enhance transcription of a given polynucleotide, the promoter sequence of the present invention may be linked to other regulatory sequences described above, such as: ATATT (element with strong root expression), AACAAAC and GCCACCTCAT (elements related to specific expression in seeds), CACGTG and CCTACC (both these sequences may be stimulated by a stress factor), amongst others (Ai-Min Wu et al., Isolation of a cotton reversibly glycosylated polypeptide (GhRGP1) promoter and its expression activity in transgenic tobacco, Journal of Plant Physiology 163 (2006) 426-435).

A "termination sequence" is a DNA sequence that signals the end of transcription. Examples of termination sequences are, but not limited to, the SV40 termination signal, the HSV tk adenylation sequence, the nopaline synthase (NOS) gene termination site of *Agrobacterium tumefasciens*, the octopine synthase gene termination site, the 19S and 35S gene termination site of CaMV, the alcohol dehydrogenase gene termination site of maize, the manopine synthase gene termination site, the beta-phaseolin gene termination site, the ssRUBISCO gene termination site, the sucrose synthase gene termination site, the gene termination site of the Subterranean clover stunt virus (SCSV) that infects *Trifolium subterranean*, the trpC gene termination site of *Aspergillus nidulans* and others similar. The present invention provides a regulatory region of isolated polynucleotides that may be used in the manipulation of plant phenotypes, combined with isolated polynucleotides incorporating these regulatory regions. More specifically, the present invention relates to a promoter or regulatory sequence that occurs naturally in cotton plants (*Gossypium hirsutum*), responsible for the expression of ubiquitin conjugating protein in this plant species. The cotton promoter isolated from the gene responsible for the expression of ubiquitin conjugating protein was named uceA 1.7 (SEQ ID NO:1) in the present invention.

The quantity of polypeptide of specific interest may be increased or reduced through the incorporation of additional copies of genes, or coding sequences, thus encoding the polypeptide operably linked to the promoter sequence of the present invention (SEQ ID NO:1), within the genome of an organism, such as a plant. Likewise, an increase or reduction in polypeptide quantities may be obtained through transformation of plant with antisense copies of these genes.

The polynucleotide of the present invention was isolated in cotton plants, and more specifically in *G. hirsutum*, but it may be synthesised alternatively using conventional synthesis techniques. Specifically, the isolated polynucleotide of the present invention includes the sequence set forth in SEQ ID NO:1; the complement of the sequence set forth in SEQ ID NO:1; the reverse complement of the sequence identified as SEQ ID NO:1; and the reverse sequence of the sequence set forth in SEQ ID NO:1.

Studies of the promoter activity of the present invention are provided in more detail in the examples enclosed with this report. Experimental data obtained with *Arabidopsis* quantifying GUS activity demonstrate that the recombinant vector containing the promoter uceA1.7 demonstrates greater GUS activity when compared to CaMVd35S promoter.

The polynucleotide of the present invention may be identified in genomic DNA sequences of plants, for which genome sequence information is available to the public, or isolated from several polynucleotide libraries, or may be synthesised using known state-of-the-art techniques (Sambrook et al., "Molecular Cloning, a laboratory manual", CSHL Press, Cold Spring Harbor, N.Y., 1989). The polynucleotide, for example, may be synthesised using automated oligonucleotide synthesizers (i.e. the Beckman DNA OLIGO 100M synthesiser) so as to obtain polynucleotide fragments of up to 50 or more nucleotides. A multitude of these polynucleotide fragments may then be linked using known state-of-the-art standard DNA manipulation techniques (Sambrook et al., "Molecular Cloning, a laboratory manual", CSHL Press, Cold Spring Harbor, N.Y., 1989). A conventional and exemplary polynucleotide synthesis technique involves the synthesis of a single-stranded polynucleotide segment, containing, for example, 80 nucleotides bases followed by the single-stranded polynucleotide segment with another segment of 85 complementary bases synthesised to produce an 'overhang' of 5 nucleotides. The subsequent segment may then be synthesized in a similar manner, with an 'overhang' of 5 nucleotides from the opposite strand. The "adhesive" overhangs, also known as cohesive ends, ensure an appropriate bond when both portions are hybridised. In this manner, the polynucleotide of this invention may be completely synthesized in vitro.

As noted above, the promoter sequence of the present invention may be used in recombinant and/or expression vectors for triggering transcription and/or expression of a polynucleotide of interest. This polynucleotide of interest may be endogenous or heterologous to an organism, such as, for example, a plant, to be transformed. The recombinant and/or expression vectors of the present invention may thus be used to modulate the levels of transcription and/or expression of a polynucleotide, for example, a wild plant gene, or it may be used to provide the transcription and/or expression of a DNA sequence not found in a wild plant, including, for example, a gene that encodes a reporter gene such as GUS.

In some forms of the present invention, the polynucleotide of interest incorporates an open reading frame that encodes the polypeptide of interest. The open reading frame is inserted in the vector in a sense orientation and a transformation using this type of genetic construction will generally result in selected polypeptide over-expression. The polypeptide of interest to be regulated by the promoter of the present invention may be inserted into vector in sense orientation, antisense orientation or even in both. A transformation with a recombinant and/or expression vector containing the promoter of the present invention regulating the expression of the polynucleotide of interest in an antisense orientation or in both orientation (sense and antisense) will generally result in reduced expression of the polypeptide of interest.

The polynucleotide of interest is linked in an operational manner as an encoding sequence in the polynucleotide promoter sequence of the present invention in a manner that a host cell is capable of transcribing a RNA activated by the promoter sequence linked to the polynucleotide of interest. The polynucleotide promoter sequence is generally located at the 5' extremity of the polynucleotide to be transcribed. The use of a constitutive promoter such as the promoter sequence for the ubiquitin conjugating protein of G. hirsutum set forth in SEQ ID NO:1 will affect the polynucleotide of interest transcription in all parts of the transformed plant.

The recombinant or expression vector of the present invention may also contain a selection marker efficient in cells of the organism, such as a plant, to allow the detection of transformed cells containing the inventive recombinant vector. These markers, that are well known, typically confer resistance to one or more toxins. An example of this marker is the nptII gene, whose expression results in resistance to kanamycin or neomycin, antibiotics that are normally toxic for plant cells in moderate concentrations. The transformed cells may thus be identified by their ability to grow in medium containing the antibiotics at issue. Other selection markers that may be used to construct recombinant and/or expression vectors containing the polynucleotide of the present invention may be, but not limited to, the hpt gene that confers resistance to the antibiotic hygromycin, the genes manA and the gene bar.

The system using the manA gene (that encodes the PMI enzyme—phosphomannose isomerase) of *Escherichia coli* (Miles & Guest, 1984 Complete nucleotide sequence of the fumarase gene fumA, of *E. coli*, Nucleic Acids Res. 1984 Apr. 25; 12(8): 3631-3642) having mannose as selective agent is one of the new systems advanced as alternatives to the first two described above (Joersbo et al., 1998; Parameters interacting with mannose selection employed for the production of transgenic sugar beet, Physiologia Plantarum Volume 105, Issue 1, Page 109. January 1999 doi: 10.1034/j.1399-3054.1999.105117.x). Plant species that do not metabolise mannose suffer severe growth inhibition when the latter is the sole source of carbon provided in the culture medium. The adverse and inhibitory effects resulting from the use of mannose are the consequence of accumulated mannose-6-phosphate which is a product of the mannose phosphorylation by a hexokinase. PMI promotes the interconversion of mannose-6-phosphate and fructose-6-phosphate thus allowing that the former be catabolyzed in the glycolytic pathway (Ferguson & Street, 1958. Análise de sistemas gene marcador/agente seletivo alternatives para seleção positiva de embriões somáticos transgênicos de mamoeiro. [Analysis of alternative gene marker/selective agent systems for positive selection of somatic transgenic embryos of Papaya plants] *Rev. Bras. Fisiol. Veg.*, 2001, vol. 13, n. 3, p. 365-372. ISSN 0103-3131. Malca et al., 1967 Advances in the selection of transgenic plants using non-antibiotic marker genes. Physiologia Plantarum Volume 111, Issue 3, Page 269. March 2001 doi: 10.1034/j.1399-3054.2001.1110301.x).

The bar gene (that encodes the PAT enzyme—phosphinothricin-N-acetyltransferase) of *Streptomyces hygroscopicus* (Murakani et al., 1986—The bialaphos biosynthetic genes of *Streptomyces hygroscopicus*: molecular cloning and characterization of the gene cluster. Molecular and General Genetics. 205: 42-50, 1986.), having gluphosinate ammonium (PPT) as selective agent is one of the herbicide tolerant gene types most widely used in genetic engineering for developing plant GMOs. PAT inactivates herbicides that contain PPT as active component through the detoxification of the latter. This detoxification is the result of the acetylation of the free amine group present in PPT and renders the latter incapable of competing in an inhibitory manner with glutamine synthase (GS). This allows the removal of toxic ammonia from plant cells through the conversion of glutamate into glutamine, with this reaction being catalysed by GS (Lindsey, 1992. Molecular cloning of ICAM-3, a third ligand for LFA-1, constitutively expressed on resting leukocytes *Nature* 360, 481-484 (3 Dec. 1992); doi:10.1038/360481a0).

Alternatively, the presence of the desired construct gene in transformed cells may be determined by other methods known in the state-of-the-art (Sambrook et al., "Molecular Cloning, a laboratory manual", CSHL Press, Cold Spring Harbor, N.Y., 1989), such as Southern and PCR.

The techniques to link the components of inventive recombinant or expression vectors in an operational manner are well known in the state-of-the-art and include the use of synthetic ligands containing one or more restriction endonuclease sites such as that described, for example, by Sambrook et al., ("Molecular Cloning, a laboratory manual", CSHL Press, Cold Spring Harbor, N.Y., 1989). Chimeric genes of the present invention may be linked to a vector having at least one replication system, such as, for example, *E. coli*, and thus, after each manipulation, these may be cloned and sequenced.

Recombinant and/or expression vectors of the present invention may be used to transform a variety of organisms including, but not limited to, plants. The plants that may be transformed using the recombinant and/or expression vectors of the present invention include monocot angiospermae (i.e. gramineae, maize, corn, oats, wheat and barley . . . ), dicot angiospernae (i.e. *Arabidopsis*, tobacco, leguminosae, alfalfa, eucalyptus and maples . . . ) and gimnospermae (i.e.

pine, White Spruce and Larch). The plant transformation protocols are well known in the state-of-the-art (Manual de transformagão genética de plantas. [Genetic Plant Transformation Manual]. Brasília: EMBRAPA-SPI/EMBRAPA-CENARGEM, Chapters 3 and 7, 1998). In a preferred embodiment, the recombinant and/or expression vectors are used to transform dicot plants. Preferably, the plant is selected from the Malvaceae family, more preferably of the species *Gossypium hirsutum*. Other plants may be transformed in a useful manner with the recombinant and/or expression vector of the present invention, including, but not limited to: *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna* and *Zea*.

The transcription termination signal and the polyadenylation region of the present invention include, but are not limited to, the SV40 termination signal, the HSV tk adenylation site, the nopaline synthase (nos) gene termination signal of *A. tumefasciens*, the termination signal of gene RNA 35S of CaMV, the termination signal of the virus attacking *Trifolium subterranean* (SCSV), the termination signal of gene trpC of *Aspergillus nidulans*, and others similar. Preferably, the gene termination used in the present invention is the gene termination that encodes the ubiquitin conjugating protein of cotton.

The recombinant and/or expression vectors of the present invention may be introduced into the desired host plant genome by a variety of conventional techniques. For example, *A. tumefasciens* mediated introduction; electroporation; protoplast fusion; injection in reproductive organs, injection in immature embryos; microinjection of plant cell protoplasts; use of ballistic methods, such as DNA coated particle bombardment, amongst others. The choice of technique will depend on plant type to be transformed. For example, dicot plants and some monocots and gymnospermae may be transformed using *Agrobacterium* Ti plasmid technology. The recombinant and/or expression vectors may be combined with appropriate T-DNA flanking regions and introduced into the conventional *A. tumefasciens* host vector. The virulence factor of the *A. tumefasciens* host will conduct the insertion of the genic constructs and adjacent marker into the DNA of the plant cell when the cell is infected by the bacteria. *A. tumefasciens* mediated transformation techniques, including disarmament and the use of binary vectors, are well described in the scientific literature (such as mentioned in patent application US 20020152501, Horsch et al. Science 233:496-498, 1984; and Fraley et al. Proc. Natl. Acad. Sci. USA 80:4803, 1983).

Microinjection techniques are well known in the state-of-the-art and well described in the scientific literature and patent documents. The introduction of recombinant and/or expression vectors using polyethylene glycol precipitations is described by Paszkowski et al. (Embo J. 3:2717-2722, 1984, and is mentioned in patent application US20020152501). Electroporation techniques are described in From et al. Proc. Natl. Acad. Sci. USA 82:5824, 1985 (as mentioned in patent application US20020152501). Ballistic transformation techniques are described in Klein et al. Nature 327:70-73, 1987 (as mentioned in patent application US20020152501). The introduction of recombinant and/or expression vectors of the present invention may be done in tissues, such as leaf tissues, dissociated cells, protoplasts, seeds, embryos, meristemic regions, cotyledons, hypocotyledons and others.

Preferably, the present invention uses transformation by *A. tumefasciens* mediated introduction using *A. thaliana* as model plant (Clough et al. "Floral dip: a simplified method for *Agrobacterium*-mediated transformation of *A. thaliana*", Plant J. 1998 December; 16(6):735-43.). However, other transformation methods may be used to insert recombinant and/or expression vectors of the present invention, such as bioballistics, that consists of a direct DNA transformation technique using micro-projectiles propelled at high speeds to implant DNA in cells [Rech, E. L.; ARAGÃO, F. J. L. Biobalística. In: Manual de transformação genética de plantas (Brasileiro, A. C. M. & Carneiro, V. T. C. Ed.) EMBRAPA Servico de Producão de Informacões SPI. 1998, 106 pp], and through pollen tube. The transformation method through pollen tube was disclosed by Zhou et al (Zhou, G., Wang, J., Zeng, Y., Huang, J., Qian, S., and Liu, G. Introduction of exogenous DNA into cotton embryos. Meth. in Enzymol. 101:433-448, 1983) and consists in applying a DNA solution in the upper part of an immature apple after pollination. With this technique, exogenous DNA is able to reach the plant ovary through the passage left by the pollen tube and integrate the zygotic cells already fertilized, but yet undivided.

Once the cells have been transformed, by any of the techniques mentioned above, the cells with the recombinant and/or expression vectors of the present invention incorporated within their genome may be selected by means of a selection marker, such as a hygromicin or a kanamynin resistant marker. The cells of the transformed plants may then be cultivated to regenerate an entire plant possessing the transformed genotype and, finally, the desired phenotype. Such regeneration techniques rely on the manipulation of certain phytohormones in tissue culture growth media, typically containing a biocide and/or herbicide marker that must be introduced together with the intended nucleotide sequence. Regeneration of plants from the culture of protoplasts is described in Evans et al. (Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985, and as mentioned in patent application US20020152501). Regeneration may also be obtained from plant calli, explants, organs, or parts of these. Such regeneration techniques are well described in the state-of-the-art, such as by Leelavathi et al. [Leelavathi et al, A simple and rapid *Agrobacterium*-mediated transformation protocol for cotton (*G. hirsutum* L.): Embryogenic calli as a source to generate large numbers of transgenic plants, Plant Cell Rep (2004) 22:465-470]. This work describes a protocol for the transformation and regeneration of cotton where the embryogenic callus containing *Agrobacterium* is cultivated under conditions of dehydration stress and antibiotic selection for three to six months in order to generate various transgenic embryos, with an average of 75 globular embryos. When observed on a selection of dishes, these embryos are cultivated and multiplied in media, following by the development of cotyledonal embryos in a embryo growth medium, in order to obtain an average of twelve plants per Petri dish from co-cultivated calli. Approximately 83% of these plants are transgenic. The plants thus transformed may be bred sexually or asexually, using methods known in the state-of-the-art, [Leelavathi et al, A simple and rapid *Agrobacterium*-mediated transformation protocol for cotton (*Gossypium hirsutum* L.): Embryogenic calli as a source to generate large numbers of transgenic plants, Plant Cell Rep, 2004, 22:465-470] to provide successive generations of transgenic plants.

The RNA production in cells may be controlled through choice of the promoter sequence, through selection of the number of functional copies or through the integration site of the polynucleotides incorporated into the host genome. An organism may be transformed using the recombinant and/or expression vectors of the present invention containing one or more open reading frames for encoding a polypeptide of interest.

The isolated polynucleotide of the present invention is also useful in genome mapping, in physical mapping and in the positional cloning of genes. The sequence identified as SEQ ID NO:1 and its variants may be used to design oligonucleotide probes and primers. These oligonucleotide probes designed using the polynucleotide of the present invention may be used to detect the presence of the ubiquitin conjugating protein promoter in any organism containing sufficiently similar DNA sequences in their cells using techniques well known in the state-of-the-art, such as dot blot DNA hybridisation techniques (Sambrook, J., Fritsch, E. F., Maniatis, T. Molecular cloning: a laboratory manual. $2^{nd}$ edition [M]. New York: Cold Spring Harbor Laboratory Press, 1989).

The oligonucleotide primers designed using the polynucleotide of the present invention may be used for PCR amplifications. The polynucleotide of the present invention may also be used to tag or identify an organism or reproductive material of the latter. This tag may be obtained, for example, by the stable introduction in an organism of a heterologous, non-functional, non-disruptive, polynucleotide identifier controlled by the polynucleotide of the present invention.

EXAMPLES

The present invention is further defined by the following examples. It should be understood that these examples, although describing a part of the invention, are provided merely for illustrative purposes, and, therefore, in no way limit the scope of the present inventions.

Customary molecular biology techniques such as the transformation of bacteria and the electrophoresis of nucleic acids in agarose gel are referred to by the common terms used to describe them. Details of the practices of these techniques well known in the state-of-the-art are described in Sambrook, et al., (Molecular Cloning, A Laboratory Manual, 2nd ed. (1989), Cold Spring Harbor Laboratory Press). Several of the solutions used in the experimental manipulations are referred to by their common names such as "Agarose", "TBE", "Miniprep", etc. The composition of these solutions may be found referring to above mentioned Sambrook, et al.

Example 1

Isolation of the DNA Promoter Sequence for the Ubiquitin Conjugating Protein Gene for *Gossypium Hirsutum*

Extraction of DNA in cotton was performed using the DNeasy plant mini Kit 50 by QIAGEN. The DNA sequence responsible for expression of the ubiquitin conjugating protein gene was isolated from cotton plants using the "Tail-PCR" technique. "Tail-PCR" (Thermal Asymmetric Inter-Laced PCR) consists in applying the PCR (Polymerase Chain Reaction) technique to allow the isolation of the DNA segments adjacent to known sequences using specific sequential primers along with small randomly degenerated primers in a manner as to thermally control amplification efficiency related to specific and unspecific products (Liu, Y. & Whittier, R. F. (1995). Thermal asymmetric interlaced PCR: Automatable amplification and sequencing of insert end fragments from P1 and YAC clones for chromosome walking. Genomics 25, 674-681.)

Interspersing high and low stringency cycles, specific products are preferably amplified over non-specific products. Three PCR reactions (primary, secondary and third reactions) were performed in sequence using three specific sequence primers on one side and a random primer on the other.

1) Primary Reaction:

200 ng of cv. IAC 98/708 genomic cotton DNA was added to 20 µl of a PCR reaction containing 20 mM Tris-HCl, 50 mM KCl, pH 8.4, (Gibco PCR buffer) 2 mM MgCl$_2$, 200 µM dNTPs, 400 nM primer UCE1 (5' GCTTGCCAATGGAA-CAT 3') (SEQ ID NO: 2), 3 µM primer AD3 (5' WGTGNAG-WANCANAG 3') (SEQ ID NO: 3), 1 U Taq DNA polymerase (Gibco). The reaction was performed in a thermocycler (Eppendorf, Mastercycler gradient) programmed to 38 cycles, with an initial stage of 1 min at 93° C., followed by the subsequent stages: 1 min at 95° C., 94° C., 55° C., 2.5 min at 72° C., return to stage 3 (1 min at 94° C.) repeat 4 times, 3 min at 25° C., 2.5 min at 72° C., 30 seconds at 94° C., 1 min at 60° C., 2.5 min at 72° C., return to the stage of 30 seconds at 94° C., repeat once, 30 seconds at 94° C., 1 min at 44° C., 2.5 min at 72° C., return to the stage of 30 seconds at 94° C., repeat 14 times, ending with 72° C. for 5 min.

2) Secondary Reaction:

1 µl of the product from the Primary Reaction was added to 20 µl of a PCR reaction containing 20 mM Tris-HCl, 50 mM KCl, pH 8.4, (Gibco PCR buffer) 2 mM MgCl$_2$, 200 µM dNTPs, 400 nM primer UCE2 (5' AGRTCCTTIAGCTCCTT 3') (SEQ ID NO: 4), 2 µM primer AD3 (5' WGTGNAGWAN-CANAG 3') (SEQ ID NO: 5), 0.6 U Taq DNA polymerase (Gibco). The reaction was performed in a thermocycler (Eppendorf, Mastercycler gradient) programmed to 13 cycles, with an initial stage of 30 seconds at 94° C., followed by the subsequent stages: 1 min at 55° C., 2.5 min at 72° C., return to initial stage and repeat once, 94° C. for 30 seconds, 44° C. for 1 min, 72° C. for 2.5 min, return to initial stage and repeat 11 times, ending with 72° C. for 5 min.

3) Third Reaction:

1 µl of the product from the Secondary Reaction was added to 20 µl of a PCR reaction containing 20 mM Tris-HCl, 50 mM KCl, pH 8.4, (Gibco PCR buffer) 2 mM MgCl$_2$, 200 µM dNTPs, 400 nM primer W4 (5' AGWGNAGWANCANAGA 3') (SEQ ID NO: 6), 0.6 U Taq DNA polimerase (Gibco). The reaction was performed in a thermocycler (Eppendorf, Mastercycler gradient) programmed to 13 cycles, with an initial stage of 30 secs at 94° C., followed by the subsequent stages: 1 min at 55° C., 2.5 min at 72° C., return to initial stage and repeat once, 94° C. for 30 segundos, 44° C. for 1 min, 72° C. for 2.5 min, return to initial stage and repeat 11 times, ending with 72° C. for 5 min.

Figure 1:
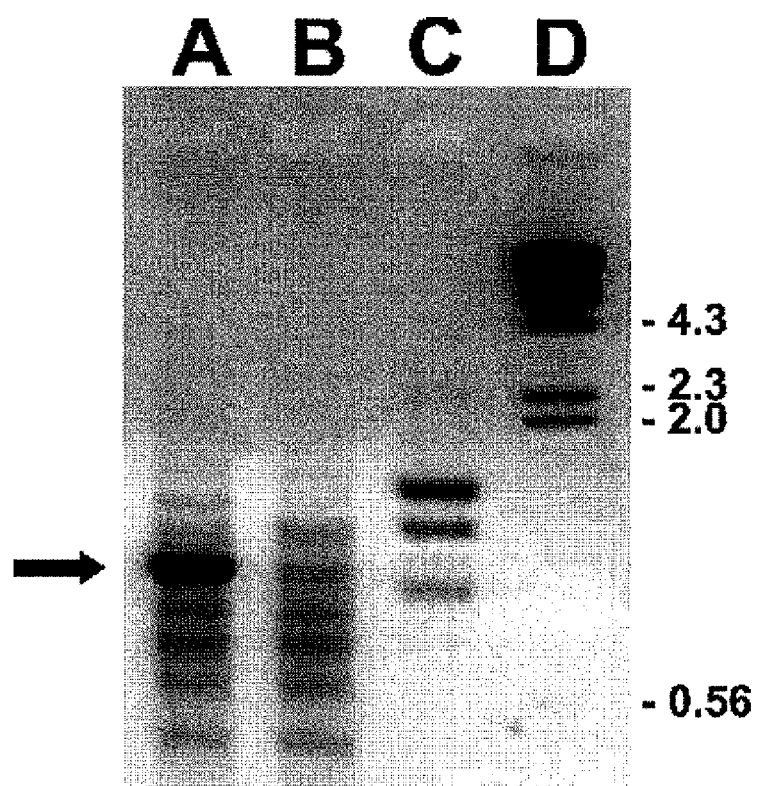
FIG. 1—Agarose gel showing the amplification product with random primer W4, producing a fragment of approximately 1.0 kb. (A) reaction with primers W4 and uce2; (B) only W4 primer control reaction; (C) only uce2 primer control reaction; (D) molecular mass marker (?/Hind III) indicated in kb. The arrow points out the potentially positive amplified fragment of approximately 1.0 kb.

Amplification with random primer W4 produced a potentially positive fragment of approximately 1.0 kb. Control reactions were made using only the random primers and the UCE2 primer based on TAIL-PCR controls. The products amplified in the reaction with the two primers (W4 and UCE2) and that are not present in the controls using only one of the primers were considered potentially positive (FIG. 1).

Figure 2:
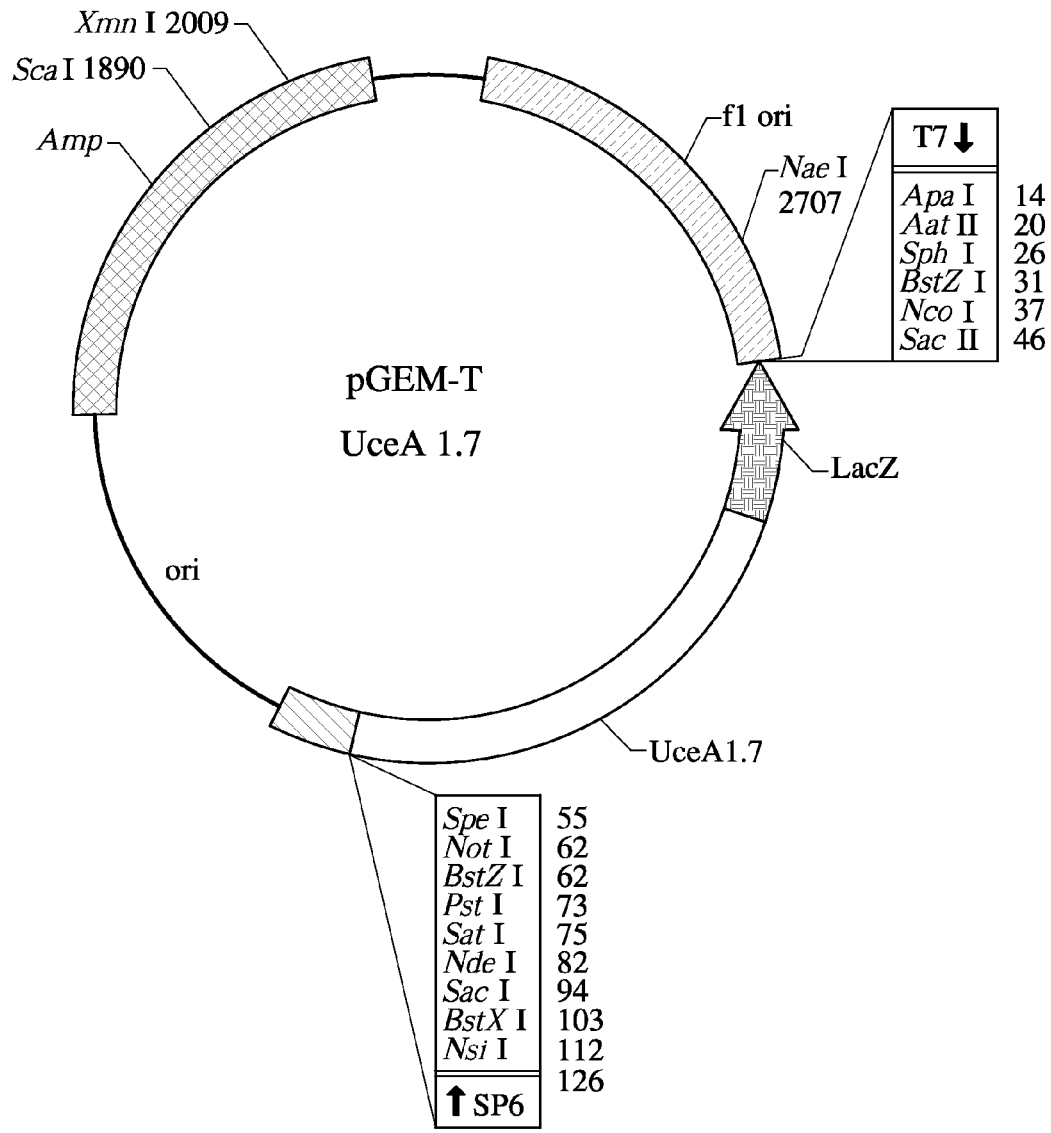
FIG. 2—pGEM-T vector linked to the 1.0 kb fragment.

The product of the PCR was submitted to electrophoresis in agarose-TBE and the 1.0 kb amplified fragment was purified using the "Gene Clean" kit (QIAGEN) and cloned into the pGEM-T (Promega) vector. The resulting recombinant vector (FIG. 2) was used to transform cells of *E. coli* by electroporation (Manual de transformação genética de plantas. [Genetic Plant Transformation Manual]. Brasília: EMBRAPA-SPI/EMBRAPA-CENARGEM, 1998. p. 101). Twelve clones were selected and their DNA were purified through small scale plasmid DNA preparation (Miniprep-Sambrook, et al., (Molecular Cloning, A Laboratory Manual, 2$^{nd}$ ed. (1989), Cold Spring Harbor Laboratory Press). Twelve clones were sequenced in an ABI automatic sequencer using T7 and SP6 primers. Sequencing was performed on Embrapa-Cenargen sequencing platform and confirmed as positive through sequencing analysis. Six clones presented the promoter in an 'antisense' orientation in relation to lacZ gene present in the vector and six presented the promoter in a 'sense' orientation in relation to lacZ gene in the vector.

The resulting sequences generated a consensus sequence with SEQ ID NO:1, based on the alignment of positive clone sequences with the cotton derived promoter sequence.

The analysis of the sequencing of the isolated cotton gene corresponding to the Leubc4 gene family revealed the existence of a segment similar to the TATA box consensus usually present in eukaryote promoters. Furthermore, comparison of the sequences obtained with other sequences found in databases did not reveal any significant similarity, and neither were any significant open reading sequences detected which therefore indicates that the region does not correspond to a coding sequence.

Example 2

The comparative analysis of the uceA1.7 promoter sequence for the ubiquitin conjugating protein of cotton with other constitutive promoters of plants showed that the uceA1.7 promoter is significantly different from other promoters described in the literature (FIG. 3A-F).

Table 1 shows relatively low sequence identities between the main constitutive promoters described in the literature and the promoter of the present invention (uceA1.7). The promoters were selected from those with the greatest identity, in accordance with searches in the NCBI databases (ncbi.nlm.nih.gov).

TABLE 1

| Constitutive promoters | Organisms | UceA1.7 (% Identity) |
| --- | --- | --- |
| Trehalose 6-phosphate synthase of A. thaliana | Arabidopsis thaliana | 38.2 |
| Uce_Oryza_3 | Oryza sativa | 20.0 |
| Gos-2_Zea | Zea mays | 27.2 |
| Uce_Oryza_1 | Oryza sativa | 40.7 |
| A-Tubulin_Coffea_1 | Coffea | 37.1 |
| Uce_Oryza_4 | Oriza sativa | 33.2 |
| UBI9_Saccharum | Saccharum | 38.8 |
| Enolase_Zea | Zea mays | 33.5 |
| Actin-2_Zea | Zea mays | 33.3 |
| Uce_Oryza_2 | Oryza sativa | 35.3 |
| A-Tubulin_Coffea_2 | Coffea | 44.3 |
| 35Sd_AMV | Alfalfa mosaic virus | 34.1 |

Table 1. Identity differences between the uceA1.7 cotton promoter and the different existing constitutive promoters.

The analysis was performed through the multiple alignment of sequences generated by the CLUSTAL_W software and pairing was done with the PAIRWISE software.

Example 3

Cloning of the uceA 1.7 Promoter Sequence of the Ubiquitin Conjugating Protein Gene of Cotton in a Plant Transforming Vector (pCAMBIA 1391)

The transformed bacteria DNA containing the recombinant vector, as such, the UCE cotton promoter cloned to vector pGEM-T was digested with the Nco I and Spe I restriction enzymes. Generally, 5 U of enzyme for every μg of DNA was used, in OPA buffer (One-Phor-All) by Pharmacia Biotech in a final concentration of 2x, at 37° C. for 3 hours. The enzymes do not cut the insert, but the flanking cloning site of the vector and the 1.0 kb insert purified with Gene Clean (Bio 101 System). Vector pCAMBIA1391 (FIG. 4) was digested with Nco I and Spe I and purified with the Gene Clean kit (Bio 101 System). The 1.0 kb insert was linked to vector pCAMBIA1391 with T4 DNA ligase (FIG. 4). The DNA concentration (vector pCAMBIA: promoter uceA1.7) used in the ligation system was performed at a molar rate of 1:3. The ligation reaction was performed in buffer of ligase 1× containing 5 U of T4 DNA ligase. The recombinant vector containing the polynucleotide of the present invention was used to transform competent cells of *E. coli* by electroporation (Manual de transformação genética de plantas. [Genetic Plant Transformation Manual]. Brasília: EMBRAPA-SPI/EMBRAPA-CENARGEM, 1998. p. 101). Eight clones were selected from a total of 400 and analysed by PCR, with W4 and UCE2 primers, to ascertain the presence of the insert. Clones 1, 6 and 7 were positive as shown in FIG. 5. To confirm cloning and ascertain the insert orientation, the plasmid DNA of clones 1 and 7 were obtained by preparation of small-scale plasmid DNA with the Miniprep kit 250 (QIAGEN) and digested with Hind III and Xba I. Generally, 5 U of enzyme for every μg of DNA was used, in OPA buffer (One-Phor-All) by Pharmacia Biotech in a final concentration of 1×, at 37° C. for 3 hours. Hind III does not cut the insert, but its site is present in the polylinker of the vector and Xba I cuts the insert at position 148. Both clones were confirmed positive as shown in FIG. 6. The pCAMBIA1391 vector was selected so that the fragment corresponding to the 5' extremity of the UCE gene present in clone uceA1.7 (uceA refers to the ubiquitin conjugating enzyme of cotton; 1.7 refers to the positive clone numbers obtained in each stage of the cloning process. The 1 corresponds to clone number 1 of the promoter amplification and the 7 to clone number 7 of the cloning of clone 1 in vector pCAMBIA1391) could be cloned in phase with the gusA gene coding region present in the vector.

Example 4

Functional Characterisation of the DNA Promoter Sequence for the Ubiquitin Conjugating Protein Gene of Cotton—uceA1.7

In order to validate the potential of the DNA sequence isolated, the vector containing the promoter sequence SEQ ID NO:1 was introduced into *A. tumefasciens* LBA 4404 cells by heat shock. This transformation involved the addition of 1 μg of plasmid DNA (pCAMBIA1391 vector, containing the promoter of the present invention) in 100 μl of suspension of *A. tumefasciens* competent cells LBA 4404, the reaction was then incubated in ice for 30 minutes. The cells remained in liquid nitrogen until solidification and were then immediately transferred to 37° C. for a further incubation of 5 minutes. 1 ml YEB medium (5 g beef extract, 1 g yeast extract, 5 g peptone, 5 g sucrose and 240 mg MgSO$_4$, made up to the 1 litre with deionised water and with the pH adjusted to 6.8) was added to the reaction. The cells were then incubated for 2 hours at 28° C. The suspension was allowed to grow on solid YEB medium (YEB medium containing agar 1.6% w/v). A positive colony produced in the YEB medium with the antibiotic of choice (kanamycin) was selected. These transformed cells were used to transform *A. thaliana*-Columbia plants through the floral bud infiltration technique. This technique consists in soaking floral buds of *A. thaliana* in a culture of *Agrobacterium* containing 50 g/l (w/v) sucrose and 300 μl/l Silwet L-77. For such, the *A. thaliana* plants were immersed upside down during 5 minutes in a culture of *Agrobacterium* transformed with the recombinant vector of the present invention, in a manner, however, that only soaks the floral buds. The plants were then cultivated in greenhouse until seeds could be harvested.

The seeds collected were first disinfected in alcohol 70% for 1 minute, then in sodium hypochlorite 1% for 15 minutes and finally washed 4 times with sterile water. The seeds were then sown in MS culture medium (Murashige, T. & Skoog, F. Physiol. Plant., 15: 473-497, 1962) containing hygromycin in a concentration of 20 μg/ml with the objective of selecting transformants (FIG. 8A). The germinating and rooted plantlets were transferred to cups containing sterile soil and covered so as to retain humidity before being transferred to greenhouses (FIG. 8B).

After several weeks, depending on the development of the acclimatised plants, cuts of roots, stems, leaves and floral buds were made and these were incubated in a solution of X-gluc prepared in accordance with Brasileiro & Carneiro (Manual de transformação genética de plantas. [Genetic Plant Transformation Manual]. Brasília: EMBRAPA-SPI/EMBRAPA-CENARGEM, 1998. p. 131) with the intent of verifying the induction of gus gene expression.

The recombinant vector containing the double CaMV35S (Cauliflower Mosaic Virus 35S promoter) with the sequence enhancer of the AMV (Alfalfa Mosaic Virus) (CaMV35SdAMV) was capable of promoting expression of the gus gene in the (a) leaves, (b) stem, (c) roots and (d) floral buds of *A. thaliana* (FIG. 9 A-D), as expected, considering that this promoter has been described in the scientific literature as a strong constitutive promoter. Thus, when comparing the present invention containing a sense construction of the uceA1.7 cotton promoter with CaMV35SdAMV, it is possible to perceive that the uceA1.7 promoter is an excellent biotechnological tool because this latter promoter also possesses strong constitutive expression promoting widespread β-glucoronidase enzymatic activity in the (e) leaves, (f) stem, (g) roots and (h) floral buds of *A. thaliana* (FIG. 9 E-H).

The strategy used in the present invention for the functional characterisation of the DNA sequences previously isolated from cotton plants was efficient to assess the potential of this sequence. The results obtained show that the uceA1.7 sequence is capable of conducting high levels of β-glucoronidase expression and thus represents a regulatory sequence having potential constitutive use for the production of genetically modified plants.

With the intent of quantitatively determining the expression conducted by the DNA sequence under study herein, a fluorimetric test was performed for specific β-glucoronidase enzyme activity using protein extracts from *Arabidopsis* plants containing the constructs (recombinant vectors) with CaMV35S (as positive control) and the uceA1.7 cotton promoter. For such, the protein extracts (were obtained in accordance with the Genetic Plant Transformation Manual (Manual de transformação genética de plantas. Brasília: EMBRAPA-SPI/EMBRAPA-CENARGEM, 1998. p. 133) They were quantified by the Bradford method (in accordance to the Manual de transformação genética de plantas. [Genetic Plant Transformation Manual]. Brasília: EMBRAPA-SPI/EMBRAPA-CENARGEM, 1998. p. 255) and submitted to 2 mM MUG (4-methyl-umbelliferyl-β-D-glucuronide) substrate and after 30 minutes of reaction at 37° C. the fluorimetric activity of the reaction was determined by means of spectrophotometric tests. The calculation of specific GUS activity was made in accordance to the Genetic Plant Transformation Manual (Manual de transformação genética de plantas. Brasília: EMBRAPA-SPI/EMBRAPA-CENARGEM, 1998. p. 136. (FIG. 7).

It can be seen that the DNA sequence containing the uceA1.7 promoter region is capable of conducting GUS expression in leaves at levels similar to the strongest commercial plant promoters currently in use (double CaMV35S with the AMV enhancer). Furthermore, the expression conducted by this fragment in stems and, more specifically, in floral buds of *A. thaliana* plants is considerably superior to that of the CaMV35Sd+AMV promoter that therefore renders the promoter of the present invention more appropriate for the production of transgenic plants by expressing genes of interest in these plant tissues.

The invention claimed is:

1. An isolated polynucleotide comprising a nucleic acid molecule selected from a group consisting of:
   (a) a polynucleotide having 100% sequence identity with SEQ ID NO:1, wherein said polynucleotide has constitutive promoter activity;
   (b) the complement of the sequence of (a);
   (c) the reverse complement of the sequence of (a); and
   (d) the reverse sequence of the sequence of (a).

2. The polynucleotide of claim 1, wherein said polynucleotide is a chimeric polynucleotide and comprises said nucleic acid molecule linked to expression enhancer or promoter sequences of interest.

3. The polynucleotide of claim 2, wherein said expression enhancer or promoter is operably linked to a polynucleotide sequence of interest.

4. The polynucleotide of claim 3, wherein said polynucleotide sequence of interest comprises an encoding region that encodes a protein of interest.

5. The polynucleotide of claim 3, wherein said polynucleotide sequence of interest is isolated from an endogenous gene.

6. The polynucleotide of claim 3, wherein said polynucleotide sequence of interest is in a sense orientation.

7. The polynucleotide of claim 2, wherein said expression enhancer sequence comprises the SV40 enhancer, the HSV-1 enhancer, the AMV enhancer, or the HPV-16 enhancer.

8. A recombinant vector comprising the chimeric polynucleotide of claim 2.

9. The recombinant vector of claim 8, operably linked to:
   (a) a polynucleotide sequence of interest; and
   (b) a termination sequence.

10. The recombinant vector of claim 9, wherein said polynucleotide sequence of interest is an encoding region.

11. The recombinant vector of claim 9, wherein said polynucleotide sequence of interest is isolated from an endogenous gene.

12. The recombinant vector of claim 9, wherein said termination sequence comprises the SV40 termination signal, the HSV TK adenylation sequence, the nopaline synthase (NOS) gene termination signal of *Agrobacterium tumefasciens*, the octopine synthase gene termination signal, the 19S and 35S gene termination signal of CaMV, the alcohol dehydrogenase gene termination signal of maize, the manopine synthase gene termination signal, the beta-phaseolin gene termination signal, the ssRUBISCO gene termination signal, the sucrose synthase gene termination signal, the gene termination signal of the virus attacking *Trifolium subterranean* (SCSV), or the trpC gene termination signal of *Aspergillus nidulans*.

13. The recombinant vector of claim 8, further comprising an expression enhancer sequence.

14. The recombinant vector of claim 13, wherein said expression enhancer sequence comprises the SV40 enhancer, the HSV-1 enhancer, the AMV enhancer, or the HPV-16 enhancer.

15. A transformed cell comprising the polynucleotide of claim 1.

16. A plant, a plant part, a propagulum, or progeny of said plant comprising the polynucleotide of claim 1.

17. The transformed cell of claim 15, wherein said polynucleotide is a chimeric polynucleotide and comprises said nucleic acid molecule linked to expression enhancer or promoter sequences of interest.

18. The transformed cell of claim 15, wherein said polynucleotide comprises a recombinant vector.

19. The plant, plant part, propagulum or progeny of claim 18, wherein said polynucleotide is a chimeric polynucleotide and comprises said nucleic acid molecule linked to expression enhancer or promoter sequences of interest.

20. The plant, plant part, propagulum or progeny of claim 18, wherein said polynucleotide comprises a recombinant vector.

21. A method for modifying gene expression in an organism comprising: stably incorporating the polynucleotide of claim 2, or the recombinant vector of claim 9 within the genome of the organism.

22. The method of claim 21, wherein said organism is a plant.

23. A method for producing a plant having a modified gene expression comprising:
    a) transforming a plant cell, tissue, organ or embryo with the chimeric polynucleotide of claim 2, or the recombinant vector of claim 8;
    b) selecting transformed cells, cell calli, embryos or seeds;
    c) regenerating mature plants from said transformed cells, cell calli, embryos or seeds; and
    selecting said mature plants having a modified gene expression compared to non-transformed plants.

24. The polynucleotide of claim 1, wherein said polynucleotide is at least 1049 nucleotides in length.

* * * * *

SEQUENCE LISTING

```
<160> NUMBER OF SEQ ID NOS: 18

<210> SEQ ID NO 1
<211> LENGTH: 1049
<212> TYPE: DNA
<213> ORGANISM: Gossypium hirsutum

<400> SEQUENCE: 1
agtgaagtag cagagataat agttattaca gtagcagtaa taaaataaaa tacattttat      60
tacaaaaaaa cgtacaagag gtccgcgaag atagccaatg agaacgcaag aagacaaccc     120
aattctccta ttttttttatt aaatatttct agaagaaagg gtaaattacg ccccacggtc     180
acaaaactat taataagatc atatatttat cactcaactt ccaaaagtta caaaatgatt     240
attaaactat tcaaaagttt tatttcaagt cattggattg ttaaaatagc atttgtatgg     300
atttccctgt tcacattgcc tacatcaatc gaagcctctc attccccttc tttttttatag    360 attaagtttt tttttataaa acaatttaaa acatcatgaa tctctgaact aaaatttaaa     420
taactttttt cttcgatctt tgacattgaa tgttaaatta acttgaatct aaggtatgtt     480
```

```
ctacttgttg ataaatacag atccatcgtg ttgatcattg aatcgtcact tggagctcac    540
tcatcggact taaaaaaaaa accttaacaa cctagtgact taaataaaac ttttgaatag    600
tttactgact attttgtaac tttttaaagt taagtgacta aaacgtgaac atactaatag    660
tttagtgacc tcggatgatt ttacccaaaa aattattatt caacctctcg tcctctcctt    720
tttacacctt tttattattt tttatttttt ctctttactt tgttttttta gctatttcca    780
gcgactacta aacaaaataa aaattagccc aggacaggag gatctctcag ctactttttc    840
tctcaaaatt tctccaatta gctctgtaat tttctatttt gtttctcttt attttagatt    900
ttttttggtc cgtgttaatc ttcgttgaag gcgatctagc tttgatttga atttcatttt    960
ttttcttttt tccttttaag atacttttt gtttgtttta gggtttaggc gatggcttca    1020
aagcggatct tgaaggagct caaggacct                                     1049
```

<210> SEQ ID NO 2
<211> LENGTH: 17
<212> TYPE: DNA
<213> ORGANISM: Gossypium hirsutum

<400> SEQUENCE: 2

```
gcttgccaat ggaacat                                                  17
```

<210> SEQ ID NO 3
<211> LENGTH: 15
<212> TYPE: DNA
<213> ORGANISM: Artificial Sequence
<220> FEATURE:
<223> OTHER INFORMATION: Random degenerate primer
<220> FEATURE:
<221> NAME/KEY: misc_feature
<222> LOCATION: 5, 10, 13
<223> OTHER INFORMATION: n = A,T,C or G

<400> SEQUENCE: 3

```
wgtgnagwan canag                                                    15
```

<210> SEQ ID NO 4
<211> LENGTH: 17
<212> TYPE: DNA
<213> ORGANISM: Gossypium hirsutum
<220> FEATURE:
<221> NAME/KEY: misc_feature
<222> LOCATION: 9
<223> OTHER INFORMATION: n = I

<400> SEQUENCE: 4

```
agrtccttna gctccctt                                                 17
```

<210> SEQ ID NO 5
<211> LENGTH: 15
<212> TYPE: DNA
<213> ORGANISM: Artificial Sequence
<220> FEATURE:
<223> OTHER INFORMATION: Random degenerate primer
<220> FEATURE:
<221> NAME/KEY: misc_feature
<222> LOCATION: 5, 10, 13
<223> OTHER INFORMATION: n = A,T,C or G

<400> SEQUENCE: 5

```
wgtgnagwan canag                                                    15
```

<210> SEQ ID NO 6
<211> LENGTH: 16
<212> TYPE: DNA

```
<213> ORGANISM: Artificial Sequence
<220> FEATURE:
<223> OTHER INFORMATION: Random degenerate primer
<220> FEATURE:
<221> NAME/KEY: misc_feature
<222> LOCATION: 5, 10, 13
<223> OTHER INFORMATION: n = A,T,C or G

<400> SEQUENCE: 6
agwgnagwan canaga                                                 16

<210> SEQ ID NO 7
<211> LENGTH: 660
<212> TYPE: DNA
<213> ORGANISM: Arabidopsis thaliana

<400> SEQUENCE: 7
gtgttcattt gatagagtct aaaatcacca cttacattga ctaaccccaa aaatttgtcc    60
taaacactaa tcaatccgaa gattataaaa tgtcgacaaa gaaaataaaa taaaatagga   120
gtctatgagt cgatggaact tatccaacta aactttaata agaatgaacc aaactcaatt   180
ttgtaataat atttaaaata cgttttttact ctctcccaga atatcccatc tctctgattc   240
caattcctcc tctctctctt tcgtctctct accccgaatt gattgtttta accccggtg    300 atcggagcaa actctctgac ggtgaccgcc ggtgatcatt ttttgtgaac ttcacttttg   360
gtaagcagct ttgacttttg ttcataatcc ttcactttta cttttcaatt ttgcttttttc   420 ctctgatctg atcttagtta ttaagctgtt gaatcgcatg atcctttctt ctctgattga   480
ttatttctaa tccttcatgg gttttatgac gaatcgtgtg ttagggattc gttttttctg   540
ggttgggttt ctaaatttgt tggtctaaga acagtgaaat tgttgtttca gtgatcccag   600
attctacact ctaaatttgt tggtctaaga acagtgaaat tgttgtttca gtgatcccag   660

<210> SEQ ID NO 8
<211> LENGTH: 386
<212> TYPE: DNA
<213> ORGANISM: Oryza sativa

<400> SEQUENCE: 8
aagctttgct ccgtgtctgc ttgggccata tacacggacc agcccaatag ccagaagcct    60
gtagctctcc atgggcccgt actcgtgcca cgtgtcaatc ctgtggttcg gtttcgtggc   120
ggttgcgttt cctcctctct cttttcttt tcatcttttt ttttcttac gacatttata   180 ggtttcgtag cggctgcgtt tcctattttc cttttctttt tctatttatt tttatgggat   240
attcgctttc gtggcggctg cgtttcctcg cccatatata agagcgggtg accacgactg   300
cggcgcggcg caccactcca ccaccaccac caccactcca ccgatcggcg agagcgcggg   360
gagatcgttc gacggcggca agatgc                                       386

<210> SEQ ID NO 9
<211> LENGTH: 480
<212> TYPE: DNA
<213> ORGANISM: Zea mays

<400> SEQUENCE: 9
attattggct gtaggattct aaaccgagcc taaatagctg gaatagctct atagccctca    60
atccaaacta atgatatcta tacttatgca actctaaatt tttattctaa aagtaatatt   120
tcatttttgt caacgagatt ctctactcta ttcacaatc ttttgaagct atatttacct   180
taaatctgta ctctataccca ataatcatat attctattat ttattttat ctctctccta   240
```

| | |
|---|---|
| aggagcatcc cccctatgtct gcatggcccc cgggtcgggt cccaatctct tgctctgcta | 300 |
| gtagcacaga agggacacta gaaatgactt gcttgactta gagtatcaga taaacatcat | 360 |
| gtttacttaa ctttaaattt gtatcggttt ctactatttt tataatattt ttgtctctat | 420 |
| agatactacg tgcaacagta taatcaacct tataatattt ttgtctctat agatactacg | 480 |

<210> SEQ ID NO 10
<211> LENGTH: 811
<212> TYPE: DNA
<213> ORGANISM: Oryza sativa

<400> SEQUENCE: 10

| | |
|---|---|
| gtcgacctga tgattatttt gttgatcatg attttctttt ggctatttga ttttttgaaa | 60 |
| gatatttttt tccctgggaa gacacctatg ggacgaagat attatgttat atatatatat | 120 |
| atatatatat atatatatat atatatatat atatatatat atatatcaca tcagtctctg | 180 |
| cacaaagtgc atcctgggct gcttcaatta taaagcccca ttcaccacat ttgcgagata | 240 |
| gtcgaaaagc accatcaata ttgagcttca ggtattttg gttgtgttgt ggttggattg | 300 |
| agtccgatat ataccaaatc aatataattc actacggaat ataccatagc catcacaact | 360 |
| ttattaattt tggtagctta agatggtata tataataacc aattaacaac tgattctaat | 420 |
| tttactacgg cccagtatct accaatacaa acaacgagt atgttttctt ccgtcgtaat | 480 |
| cgtacacagt acaaaaaaac ctggccagcc tttcttgggc tggggctctc tttcgaaagg | 540 |
| tcacaaaacg tacacggcag taacgcccctt tgctgcgtgt taacggccac caacccccgcc | 600 |
| gtgacgaaac ggcatcagct ttccacctcc tcgatatctc cgcggcgccg tctggacccg | 660 |
| ccccctttcc gttcctttct ttccttctcg cgtttgcgtg gtggggacgg actcccccaaa | 720 |
| ccgcctctcc ctctctttat ttgtctatat tctcactggg ccccacccac cgcacccctg | 780 |
| ggcccactca cgagtccccc cctcccgacc t | 811 |

<210> SEQ ID NO 11
<211> LENGTH: 1671
<212> TYPE: DNA
<213> ORGANISM: Coffea

<400> SEQUENCE: 11

| | |
|---|---|
| aaaagttgta gcgggagggc tggacgatgc gtggagcgga aaatgctgga gtattggacc | 60 |
| accaaccaaa caaatagtt ttagtatatg gggtttcgaa cttccagtc aacctacaac | 120 |
| aatctgcttc tataaacaat aataaaagag taattaaatt actggtagcg ttggtgtatt | 180 |
| tggatttgcc agctttgctt ccaaactcat atcatcaatt tgatagcact tggatacgga | 240 |
| gatcgctttt gtctgcctta gtatgatatg attgctcacc cgctgtagac atgatttaaa | 300 |
| ggaaaataac acaaatatat atatataaga ccaacaaatt ataactgaaa acttttcagt | 360 |
| aatgttaatt ctaacacatg tgactagacc tgctatcatc agctgcaatt ctagaggaaa | 420 |
| cttggaccag atcagaagtt gtaaagggct gcagtccatt cctgcactat tcagtttgca | 480 |
| ggtagatggg tggaccatta tatggatctg gtccagcgtg aatgcagttg tagtaaagac | 540 |
| atgttggatt tgttatggat caaactacta ctagtaggga aatgcttcaa agacttctct | 600 |
| tgtgattttc tcccagccga atggtccaag tacactagca aaagaagcac aaacggtacc | 660 |
| aatgactcga gcgagctgac attttgggct tcagattagc acaagacaaa aggatttttc | 720 |
| acttttcttc tgtaggtgat cctggactcg caggttggca tgctcaattc aggagctttt | 780 |
| gagattggat agggtgttgg ttatgaatgc accgcaggtt gcatgctcaa ttcagagccc | 840 |

```
ttcacatgta accgtgtgta gcccaggccc aaatgccccg gaaytttaaa ctgaaatctc      900
ggaayagcag atggcaacgg tcgtaattcg tcaagcaatc cgaaacgtcg ccacaccccc      960
acgccagctg aaaatcagt tcaaaattca aaattcattt tggagccgtt caaacaaaat     1020
tgtttcagtt ttgcccctcg cctgctgccc taatcttacc ccgccattgg ggcttggatt    1080
actcgctcca gtctatatat ataactccct cccgcattgc ctcaccacac gaccccaagt    1140
cctctccttc ttctccttc ccagatccg gaggtctctc actcttccga tccagagacg     1200
tctttgtata cgcctctggt atctccattc ctccttttc cctctcttcc aaaaatctcc    1260
tattcatttc tcaaaacatc gcgaaaatga gagagtgcat ctccatccat attggtcagg    1320
ccggtatcca ggtcggaaat gcctgctggg agctctactg cctcgagcac ggcatccagg    1380
taaattgcct tctatctaac ctcttatatt tcagatctgc tgtttctctc atttttgttc    1440
aaggaaatga ttcatctttg gtttgatttt gggtgttgtg aatagcctg atggacaaat     1500 gccgagcgac cacccgtcg gaggcggaga cgacgctttc aacaccttct tcagcgaaac    1560
cggagccggc aaacacgttc ctcgtgccgt gttcgtcgat ctggagccca ctgtcatcga    1620
tgaagtccga accggcacct accgccaact cttccaccct gagcagctca t             1671

<210> SEQ ID NO 12
<211> LENGTH: 594
<212> TYPE: DNA
<213> ORGANISM: Oriza sativa

<400> SEQUENCE: 12
aagcttgtct gtctctacta gataccaggg tttcatcttt cggtttggtc atttggacca      60
gggtgcccga aatatcgaaa tttcagaaat ttcggttcga aattatatga atttttgaac     120
aaaatttgat taaattaaac aaaatatatt cagatttgca aaaatatga aaaaaaaatc      180 ggtcgaaata atgtcgtatc tgggttcgat ccgaaatttt gaacccatgc tagctgccag     240
gctttggatt ctgagcgtca cgtcaggcac aataaaatat ttgggcctct aactcttcgt     300
gggctgatct gggccgtagc agacgagaga cgccatgaca cgatctcatc aattccgtag     360
tggccacgga actcacgtag cgcaaatgcc gctcccgttt ccgcatcgtg cgatttatct     420
cctttctgtt tccgaatttt attagtagtt gcgatattat taatacaggt ctcgtagcgg     480
ccgcgtctcc cctcccctta tataaaggca gcgtttctgc aagttattac ccaatctaca    540
cgagagagag atcgttcgac gcatatagag agagagagag atagggcaag atgc           594

<210> SEQ ID NO 13
<211> LENGTH: 1080
<212> TYPE: DNA
<213> ORGANISM: Saccharum

<400> SEQUENCE: 13
gaattccggc gtgggcgctg ggctagtgct cccgcagcga gcgatctgag agaacggtag      60
agttccggcc gggcgcgcgg gagaggagga gggtcgggcg gggaggatcc gatggccggg     120
aacgagtgga tcaatgggta cctggaggcg atcctcgaca gccacacctc gtcgcgggt     180 gccggcggcg gcggcggcgg gggggacccc aggtcgccga cgaaggcggc gagcccccgc     240
ggcgcgcaca tgaacttcaa cccctcgcac tacttcgtcg aggaggtggt caagggcgtc     300
gacgagagcg acctccaccg gacgtggatc aaggtcgtcg ccacccgcaa cgcccgcgag     360 cgcagccacca ggctcgagaa catgtgctgg cggatcggc acctcgcgcg caagaagaag    420
cagctggagc tggagggcat ccagagaatc tcggcaagaa ggaaggaaca ggagcaggtg     480
```

```
cgtcgtgagg cgacggagga cctggccgag gatctgtcag aaggcgagaa gggagacacc      540
atcggcgagc ttgcgccggt tgagacgacc aagaagaagt tccagaggaa cttctctgac      600
cttaccgtct ggtctgacga caataaggag aagaagcttt acattgtgct catcagcgtg      660
catggtcttg ttcgtggaga aaacatggaa ctaggtcgtg attctgatac aggtggccag      720
gtgaaatatg tggtcgaact tgcaagagcg atgtcaatga tgcctggagt gtacagggtg      780
gacctcttca ctcgtcaagt gtcatctcct gacgtggact ggagctacgg tgagccaacc      840
gagatgttat gcgccggttc caatgatgga gaggggatgg gtgagagtgg cggagcctac      900
attgtgcgca taccgtgtgg gccgcgggat aaatacctca agaaggaagc gttgtggcct      960
tacctccaag agtttgtcga tggagccctt gcgcatatcc tgaacatgtc caaggctctg     1020
ggagagcagg ttggaaatgg gaggccagta ctgccttacg tgatacatgg gcactatgcc     1080
```

<210> SEQ ID NO 14
<211> LENGTH: 600
<212> TYPE: DNA
<213> ORGANISM: Zea mays

<400> SEQUENCE: 14

```
tcatatattt atgaacggag atagtgcatc tatcatgcga ttcttcgacg gagtcgacgt       60
ctgattggac cagaatttca gatggtgagc aaaagtgcca cttgcctgcc tccttttctc      120
gtgcctgcct caaggataga aagaaaggag aaacaatata ctatttaaga tcagataaaa      180
tattataagt caaggataga aagaaaggag aaacaatata ctatttaaga tcagataaaa      240
aaagagctaa taattttttg ggacacatat actggttaca ttgttataat ctgtatatat      300
cacgttgttc gaatatattc caaattttta ctatgattcg tgctctaccg gaactacttc      360
tagattttga aaactttatg agaattttct tatttagata cactaaggct aattttggtt      420 ggttttggc tcgctagcta ccattacctc ctgcatctag acattacaaa tttacaataa      480
ataaagttcc tagattttga acgaaaccag cagagcgcac accgtccttg ccccacggaa      540
caagaaaaat ggaatatgct cccgcagccc tcgtggaaac caagggcgga ccttcccctc      600
```

<210> SEQ ID NO 15
<211> LENGTH: 613
<212> TYPE: DNA
<213> ORGANISM: Zea mays

<400> SEQUENCE: 15

```
tcagtatgat tgctttcaat ataggctgat ggagcctatg aatgatctat aactatgtga       60
ttggatgtct taacttgcgt agccaagctc gtatgagcct cttttactgg gtaccactaa      120
tttctatata ttagatacag ttaaataagt ctaaattaca tcggtgcgtg cgtgccagta      180
cgactagatg tagtgaacta acacaggtt aagctgtgat caatgtatgt agagagtctg      240
actctttata tgcggacaac taaacacacg ataagtgtcg agaatgattg aggaaatatt      300
ggtcgttcca cgtgattgag taagaatgag agggaaataa aaggatttgg tgcgttggtt      360
ttgaaggcag gatttggtta ggatgggtgg acgtttgaag tgatgagttt ttcaagcgta      420
tagattttct atttgtcctt tttaattaac tttctcccag ccgggatgcg cgtataaaaa      480
ccggcgaaac ccttggctct cctcattcgg cctatcacaa ccgcttactc tcgtgcgctc      540
tccgtgggag cgaggacccg cggccggcgg cagcggcagc ttctcctaga tctccggcat      600
catcagtgga tcc                                                         613
```

<210> SEQ ID NO 16

<211> LENGTH: 1712
<212> TYPE: DNA
<213> ORGANISM: Oryza sativa

<400> SEQUENCE: 16

```
ctgcagaaat gcaaatttca taaaacaaac tactagtact gtttgttcat tggtcttatc      60
caaaacttag ccactgcaac aagttcttga accttagcac aatcatattg tgcatgcact     120
tgtttattgc aaagaatggt gcgtagggaa cacgcatgat ttttgaattg ctggcacata     180
attttatcat tagaaactgg aatgcaacat gtacccttg tcatggtttc tttccgagac      240
attgcactgt ttttttaat cctatcatta tcataatgcc aagaactggt caccaaccag      300
cattttgcat catggttagt tgagctgtcc ccatgtatca ataggtgcat tgtattggtc     360
caaaatataa atgcagtgga tgcaacctat ctcatggccg tcaacaaaag aaatcaaaag     420
ggaaatgcac catcttatat ctccagttta tatgaacaga ttggataaga tcataagatc     480
aagtggttta tattattttg aggaaatataa catggattca tcctaatcac tcgtctaggc     540
agtatgtgta ttcatgatgg atatggtact atactacgga gttttttctt cacaaaataa     600
cctgttattt tgacctccaa ccaaacacga attataccaa aaattgggtt atttcatcta     660
tagtacaact ctattataaa catgcagtaa attatcctac acatatacca aaattcaagt     720
gtaataatcc taatacacag acttaaaaat caaactatt ccttttaag atatggaaaa       780
ccatttttt aacggaagga aaacaaattc gggtcaaggc ggaagccagc gcgccacccc       840
acgtcagcga atacggaggc gcggggttga cggcgtcacc cggtcctaac ggcgaccaac     900
aaaccagcca gaagaaatta cagtaaaaaa aagtaaattg cactttgacc cacctttat     960
tacccaaagt ttcaatttgg accacccta aacctatctt ttcaaattgg gccgggttgt    1020
ggtttggact accatgaaca actttcgtc atgtctaact tccctttcgg caaacatatg    1080
aaccatatat agaggagatc ggccgtatac tagagctgat gtgtttaagg tcgttgattg    1140
cacgagaaaa aaaatccaa atcgcaacaa tagcaaattt atctagttca aagtgaaaag    1200
atatgtttaa aggtagtcca aagtaaaact tagggggctgt ttggttccca gccatacttt    1260
accattactt gccaacaaaa gttgccacac cttgtctaag gtgaggtgat caaattgtta    1320
gccacaactt actaagccta agggaatctt gccacacttt tttgagccat tgacacgtgg    1380
gagtgaattt gttagaggga aatcttgcca caactgtggc tacaaccaaa cacctgtcaa    1440
atttgcctaa ccttaggcgt ggcaaactgt ggcaaagtgt ggcttacaac caaacacacc    1500
cttagataat aaaatgtggt ccaaagcgta attcactaaa aaaaaatcaa cgagacgtgt    1560
accaaacgga gagcaacggc atcttctcga aatttcccaa ccgctggctg gcccgcctcg    1620
tcttcccgga aaccgcggtg gtttcagcgt ggcggattct ccaagcagac ggagacgtca    1680
cggcacggac tcctcccacc acccaaccgc ca                                  1712
```

<210> SEQ ID NO 17
<211> LENGTH: 919
<212> TYPE: DNA
<213> ORGANISM: Coffea

<400> SEQUENCE: 17

```
catttcttgc cagaaagcac tagtgaatat tctatccctg tcagtcacta tagattctgg      60
aagtccatgt aatctaaaaa tgtttccagg aagagttgag ccacctgttt ggttgtgaag     120
gggtgagcta aggcaagcaa atgacctact ttggacaacc tatcaatcac gtattatatc     180
cttgagattc tggaaggctc tctatgaagt ccatggttag gtgagtccaa gctaaacgag     240
```

```
gaataggtga tggttgtagc agtccaaggt agggtccatg ctttgactta aatctttggc    300
atatgtcaca agcatgaata tacctgatga ttttccccaa atgttttga ggttttaat     360 accgggaatg gcccaggaaa aagggccctg gctttgcacc aaggtcccct aagaatttct    420
ggcaaaagtt caagcggttc caaagtgccc caatgggacc tctccaaaaa aggtgccccg    480
gggacaagtt gtgctcagtt cggcgcgttt caagacaggt tttggccaga aagcaaaggg    540
gttccaaagg gtgtcagagg gtccatgttt caaaactccg ggtgtcttgg tcccccataa    600
ttgacttcgg ctaagtaaag gaaaaccta gccgaggctg taattaagcc gaagtcctaa     660
cgcgatggcg aacggccgag gtggtcggag cctaagagac ataggcggga ccccagctct    720
gccgacctgg aaataccctc ctcatatacc attactagtt agtagtcacc actgctactg    780
cttcagttcc ttttatcact tgctttacat gaattaagtc gatgctcttc cttgaataac    840
tagcgattag tttcgtggtg acctatctag ccattttttct gtttgggtgg catcaatcct   900
gaacacagaa agctgcaag                                                 919

<210> SEQ ID NO 18
<211> LENGTH: 653
<212> TYPE: DNA
<213> ORGANISM: Alfalfa mosaic virus

<400> SEQUENCE: 18
ggtccgatct gagactttc aacaaagggt aatatcggga aacctcctcg gattccattg     60
cccagctatc tgtcacttca tcaaaaggac agtagaaaag gaaggtggca cctacaaatg    120
ccatcattgc gataaaggaa aggctatcgt tcaagatgcc tctgccgaca gtggtcccaa    180
agatggaccc ccacccacga ggagcatcgt ggaaaaagaa gacgttccaa ccacgtcttc    240
aaagcaagtg gattgatgtg atggtccgat ctgagacttt tcaacaaagg gtaatatcgg    300
gaaacctcct cggattccat tgcccagcta tctgtcactt catcaaaagg acagtagaaa    360
aggaaggtgg cacctacaaa tgccatcatt gcgataaagg aaaggctatc gttcaagatg    420
cctctgccga cagtggtccc aaagatggac cccacccac gaggagcatc gtggaaaaag    480
aagacgttcc aaccacgtct tcaaagcaag tggattgatg tgatatctcc actgacgtaa    540
gggatgacgc acaatcccac tatccttcgc aagacccttc ctctatataa ggaagttcat    600
ttcatttgga gaggagatct ttttattttt aattttcttt caaatacttc cac           653
```